(12) United States Patent
Behar et al.

(10) Patent No.: US 12,083,111 B2
(45) Date of Patent: *Sep. 10, 2024

(54) USE OF HEXOKINASE 2/MITOCHONDRIA-DETACHING COMPOUNDS FOR ACTIVATING IMMUNE RESPONSES

(71) Applicant: Vidac Pharma Ltd., Ness Ziona (IL)

(72) Inventors: Vered Behar, Bet Zayit (IL); Oren Menahem Becker, Mevasseret Zion (IL); Reut Yosef Hamo, Ramot Meir (IL); Eyal Dor-On, Ramat Hasharon (IL)

(73) Assignee: Vidac Pharma Ltd .., Rehovot (IL)

( * ) Notice: Subject to any disclaimer, the term of this patent is extended or adjusted under 35 U.S.C. 154(b) by 255 days.

This patent is subject to a terminal disclaimer.

(21) Appl. No.: 17/403,936

(22) Filed: Aug. 17, 2021

(65) Prior Publication Data

US 2021/0369697 A1 Dec. 2, 2021

Related U.S. Application Data

(60) Continuation of application No. 16/775,279, filed on Jan. 29, 2020, now Pat. No. 11,096,935, which is a division of application No. 15/576,824, filed as application No. PCT/IL2017/051213 on Nov. 7, 2017, now Pat. No. 10,682,346.

(60) Provisional application No. 62/573,179, filed on Oct. 17, 2017, provisional application No. 62/418,323, filed on Nov. 7, 2016.

(51) Int. Cl.
| | |
|---|---|
| *A61K 31/47* | (2006.01) |
| *A61K 9/00* | (2006.01) |
| *A61K 9/06* | (2006.01) |
| *A61K 31/496* | (2006.01) |
| *A61K 31/506* | (2006.01) |
| *A61K 35/17* | (2015.01) |
| *A61K 39/395* | (2006.01) |
| *A61K 45/06* | (2006.01) |
| *A61P 35/00* | (2006.01) |
| *A61P 37/04* | (2006.01) |

(52) U.S. Cl.
CPC ............ *A61K 31/47* (2013.01); *A61K 9/0014* (2013.01); *A61K 9/0019* (2013.01); *A61K 9/0029* (2013.01); *A61K 9/0053* (2013.01); *A61K 9/06* (2013.01); *A61K 31/496* (2013.01); *A61K 31/506* (2013.01); *A61K 35/17* (2013.01); *A61K 39/39558* (2013.01); *A61K 45/06* (2013.01); *A61P 35/00* (2018.01); *A61P 37/04* (2018.01)

(58) Field of Classification Search
CPC .................................................. A61K 31/47
See application file for complete search history.

(56) References Cited

U.S. PATENT DOCUMENTS

| | | | |
|---|---|---|---|
| 9,284,252 B2 | 3/2016 | Herzberg et al. | |
| 9,284,274 B2 | 3/2016 | Cashman et al. | |
| 11,084,807 B2* | 8/2021 | Salama | C07D 335/14 |
| 11,096,935 B2* | 8/2021 | Behar | A61K 35/17 |
| 2004/0097734 A1 | 5/2004 | Gerlach et al. | |
| 2013/0089615 A1 | 4/2013 | Fehr Pereira Lopes | |
| 2013/0203689 A1 | 8/2013 | Kashman et al. | |
| 2015/0307564 A1 | 10/2015 | Young | |

FOREIGN PATENT DOCUMENTS

| | | |
|---|---|---|
| WO | WO 2005/054172 A2 | 6/2005 |
| WO | WO 2007/066336 A2 | 6/2007 |
| WO | WO 2007/066337 A2 | 6/2007 |
| WO | WO 2008/111088 A2 | 9/2008 |
| WO | WO 2010/143180 A1 | 12/2010 |
| WO | WO 2014/143180 A1 | 9/2014 |
| WO | WO-2017/168416 A1 | 10/2017 |
| WO | WO 2018/033918 A1 | 2/2018 |
| WO | WO 2018/083705 A1 | 5/2018 |

OTHER PUBLICATIONS

Arbel et al. "Mediation of the antiapoptotic activity of Bcl-XL protein upon interaction with VDAC1 protein" *J Biol Chem.* 2012;287(27):23152-23161.
Batlevi et al. CAS: 167: 174048, 2015.
Behar, Vered, et al. "A Hexokinase 2 Modulator for Field-Directed Treatment of Experimental Actinic Keratoses" *J Invest Dermatol.* 2018;138(12):2635-2643.
Berge et al. "Pharmaceutical salts" *J Pharm Sci.* 1977;66(1):1-19.
Buchwald et al. "Long-term, continuous intravenous heparin administration by an implantable infusion pump in ambulatory patients with recurrent venous thrombosis" *Surgery.* Oct. 1, 1980;88(4):507-16.
Chaqour et al. "Chronic UVB-and all-trans retinoic-acid-induced qualitative and quantitative changes in hairless mouse skin" *J Photochem Photobiol B* 1995;28(2):125-135.
Cozzi et al. "Ingenol mebutate field-directed treatment of UVB-damaged skin reduces lesion formation and removes mutant p53 patches" *J Invest Dermatol.* 2012;132(4):1263-1271.
Definition of immunocompromised, Cancer. Gov website (https://www.cancer.gov/publications/dictionaries/cancer-terms/def/immunocompromised), accessed 2019. (year: 2019).
Dinkova-Kostova et al. "A dicyanotriterpenoid induces cytoprotective enzymes and reduces multiplicity of skin tumors in UV-irradiated mice" *Biochem Biophys Res Commun.* 2008;367(4):859-865.
Fiebig et al. "Cgp 6809—A new nitrosoureido-sugar derivative with activity in human tumor xenografts" *Cancer Chemother Pharmacol.* 1989;23(6):337-340.

(Continued)

*Primary Examiner* — Rei Tsang Shiao
(74) *Attorney, Agent, or Firm* — Mark S. Cohen; PEARL COHEN ZEDEK LATZER BARATZ LLP

(57) ABSTRACT

The present invention provides methods of use of hexokinase 2 (HK2)/mitochondria-detaching compounds, including jasmonate derivatives and piperazine derivatives and pharmaceutical compositions including such compounds for inducing immune responses in a subject, including potentiating the immune response to hyperproliferative disorders such as cancer and potentiating the immune response to infectious diseases.

29 Claims, 9 Drawing Sheets

(56) References Cited

OTHER PUBLICATIONS

Fukunaga et al. "Evaluation of esophageal cancers using fluorine-18-fluorodeoxyglucose PET" J Nucl Med. 1998;39(6):1002-1007.
Goldin et al. "Methyl jasmonate binds to and detaches mitochondria-bound hexokinase" Oncogene. 2008;27(34):4636-4643.
Gottlob et al. "Inhibition of early apoptotic events by Akt/PKB is dependent on the first committed step of glycolysis and mitochondrial hexokinase" Genes Dev. 2001;15(11):1406-1418.
Hampton et al. "NAGging Hexokinase PEPs up NLRP3" Cell Host Microbe. 2016;20(2):130-132.
Harvima et al. "Mast cells as regulators of skin inflammation and immunity" Acta Derm Venereol. 2011;91(6):644-650.
Hay, Nissim. "Reprogramming glucose metabolism in cancer: can it be exploited for cancer therapy?" Nat Rev Cancer. 2016;16(10):635-649.
International Search Report for PCT Application No. PCT/IL2017/051214 dated Feb. 11, 2018.
John et al. "Subcellular localization of hexokinases I and II directs the metabolic fate of glucose" PLoS One. 2011;6(3):e17674. Published Mar. 9, 2011.
Kim et al. "mTOR-targeted therapy: differential perturbation to mitochondrial membrane potential and permeability transition pore plays a role in therapeutic response" Biochem Biophys Res Commun. 2014;447(1):184-191.
Kligman et al. "Histogenesis and progression of ultraviolet light-induced tumors in hairless mice" J Natl Cancer Inst. 1981;67(6):1289-1293.
Kolho et al. "Hepatitis C antibodies in dialysis patients and patients with leukaemia" J Med Virol. 1993;40(4):318-321.
Krasnov et al. "Targeting VDAC-bound hexokinase II: a promising approach for concomitant anti-cancer therapy" Expert Opin Ther Targets. 2013;17(10):1221-1233.
Kvansakul et al. "The Bcl-2 family: structures, interactions and targets for drug discovery" Apoptosis. 2015;20(2):136-150.
Lee et al. CAS: 158:205499, 2013.
Li et al. "Deguelin inhibits non-small cell lung cancer via down-regulating Hexokinases II-mediated glycolysis" Oncotarget. 2017;8(20):32586-32599.
Li et al. "Benserazide, a dopadecarboxylase inhibitor, suppresses tumor growth by targeting hexokinase 2" J Exp Clin Cancer Res. 2017;36(1):58. Published Apr. 20, 2017.
Lin, Hong, et al. "Discovery of a novel 2, 6-disubstituted glucosamine series of potent and selective hexokinase 2 inhibitors." ACS Med Chem Lett. 2015;7(3):217-222. Published Dec. 28, 2015.
Lis et al. "The HK2 dependent 'Warburg effect' and mitochondrial oxidative phosphorylation in cancer: targets for effective therapy with 3-bromopyruvate" Molecules. 2016;21(12):1730. Published Dec. 15, 2016.
Lunt et al. "Aerobic glycolysis: meeting the metabolic requirements of cell proliferation" Annu Rev Cell Dev Biol. 2011:27:441-464.
Madan et al. "Non-melanoma skin cancer" Lancet. 2010;375(9715):673-685.
Majewski et al. "Hexokinase-mitochondria interaction mediated by Akt is required to inhibit apoptosis in the presence or absence of Bax and Bak" Mol Cell. 2004;16(5):819-830.
Mathupala et al. "Hexokinase-2 bound to mitochondria: cancer's stygian link to the "Warburg Effect" and a pivotal target for effective therapy" Semin Cancer Biol. 2009;19(1):17-24.
Mishra et al. CAS: 140: 74883, 2003.
Oppel et al. "Actinic keratosis: the key event in the evolution from photoaged skin to squamous cell carcinoma" Skin Pharmacol Physiol. 2004;17(2):67-76.
O'Sullivan et al. "When hexokinase gets that NAG-ing feeling . . . " Cell Metab. 2016;24(2):198-200.
Oyama et al. "Increased number of mast cells in the dermis in actinic keratosis lesions effectively treated with imiquimod" J Dermatol. 2017;44(8):944-949.
Pastorino et al. "Regulation of hexokinase binding to VDAC" J Bioenerg Biomembr. 2008;40(3):171-182.
Pastorino et al. "Mitochondrial binding of hexokinase II inhibits Bax-induced cytochrome c release and apoptosis" J Biol Chem. 2002;277(9):7610-7618.
Patra et al. "Hexokinase 2 is required for tumor initiation and maintenance and its systemic deletion is therapeutic in mouse models of cancer" Cancer Cell. 2013;24(2):213-228.
Pedersen et al. "Mitochondrial bound type II hexokinase: a key player in the growth and survival of many cancers and an ideal prospect for therapeutic intervention" Biochim Biophys Acta. 2002;1555(1-3):14-20.
Pedley et al. "Direct observation of hexokinase translocation in stimulated macrophages" The Biochemical journal. Apr. 15, 1993;291(Pt 2):515-22.
Peng et al. "Aberrant expression of the glycolytic enzymes aldolase B and type II hexokinase in hepatocellular carcinoma are predictive markers for advanced stage, early recurrence and poor prognosis" Oncol Rep. 2008;19(4):1045-1053.
Phillips et al. "Curcumin inhibits UV radiation-induced skin cancer in SKH-1 mice" Otolaryngol Head Neck Surg. 2013;148(5):797-803.
Rebel et al. "Early p53-positive foci as indicators of tumor risk in ultraviolet-exposed hairless mice: kinetics of induction, effects of DNA repair deficiency, and p53 heterozygosity" Cancer Res. 2001;61(3):977-983.
Rho et al. "Expression of type 2 hexokinase and mitochondria-related genes in gastric carcinoma tissues and cell lines" Anticancer Res. 2007;27(1A):251-258.
Röwert-Huber et al. "Actinic keratosis is an early in situ squamous cell carcinoma: a proposal for reclassification" Br J Dermatol. 2007;156 Suppl 3:8-12.
Saad & Hotte "Guidelines for the management of castrate-resistant prostate cancer". Can Urol Assoc J. 2010;4(6):380-384.
Sadelain et al. "The basic principles of chimeric antigen receptor design" Cancer Discov. 2013;3(4):388-398.
Saudek et al. "A preliminary trial of the programmable implantable medication system for insulin delivery" N Engl J Med. 1989;321(9):574-579.
Seton-Rogers "Tumour immunology: An exhausting metabolic competition" Nat Rev Cancer. 2015;15(10):573.
Shoshan-Barmatz et al. "The mitochondrial voltage-dependent anion channel 1 in tumor cells" Biochim Biophys Acta. 2015:1848(10 Pt B):2547-2575.
Shoshan-Barmatz et al. "VDAC1: from structure to cancer therapy" Front Oncol. 2012;2:164. Published Nov. 29, 2012.
Smith "Mammalian hexokinases and their abnormal expression in cancer" Br J Blomed Sci. 2000;57(2):170-178.
Ting et al. "Reactivity of autolymphocytotoxic antibodies from dialysis patients with lymphocytes from chronic lymphocytic leukemia (CLL) patients" Transplantation. 1978;25(1):31-33.
"Vidac Pharma Initiates Phase I Clinical Trial with its Novel Vdac/Hk2 Modulator", Feb. 25, 2016 (retrieved from: http://www.vidacpharma.com/news/64-vidac-pharma-initiates-phase-i-clinical-trial-with-its-novel-vdac-hk2-modulator) Feb. 25, 2016.
Wilson JE. "Isozymes of mammalian hexokinase: structure, subcellular localization and metabolic function" J Exp Biol. 2003;206(Pt 12):2049-2057.
Wolf et al. Hexokinase is an innate immune receptor for the detection of bacterial peptidoglycan Cell. 2016;166(3):624-636.
Zalaudek et al. "Morphologic grading and treatment of facial actinic keratosis" Clin Dermatol. 2014;32(1):80-87.

* cited by examiner

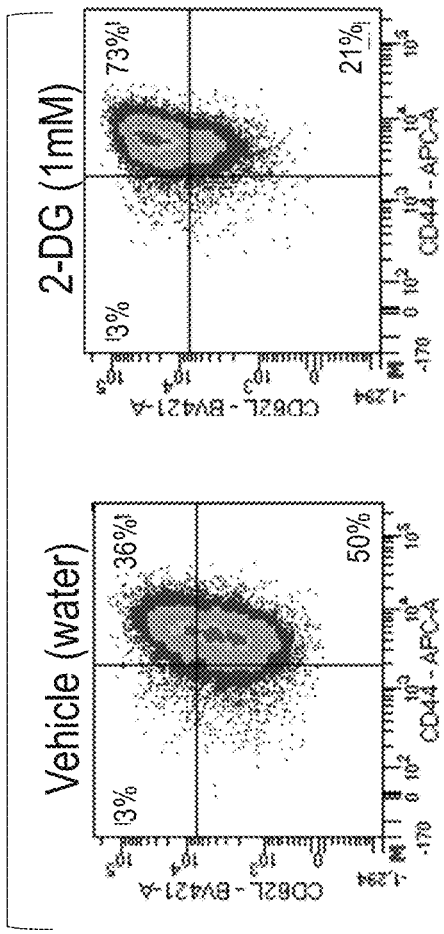
Figure 7B
Figure 7C
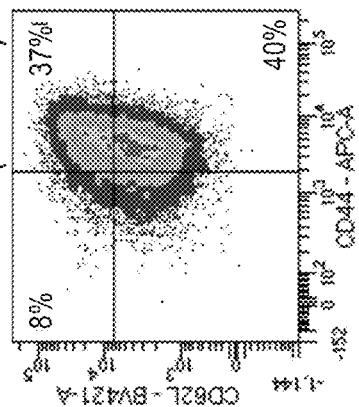
Figure 7D
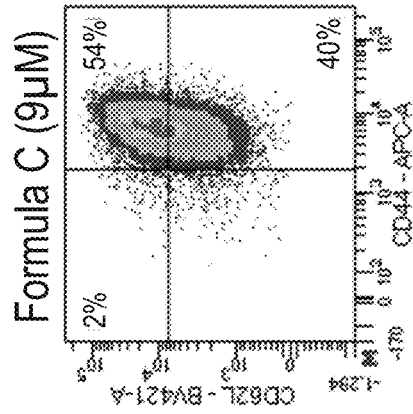
Figure 7E
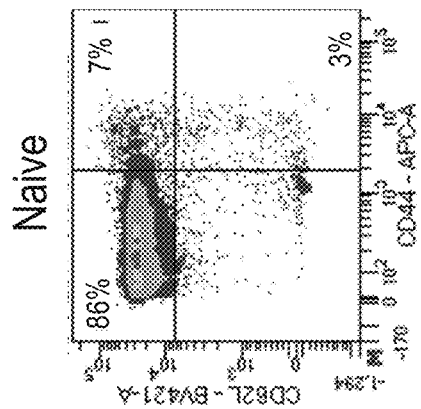
Figure 7A

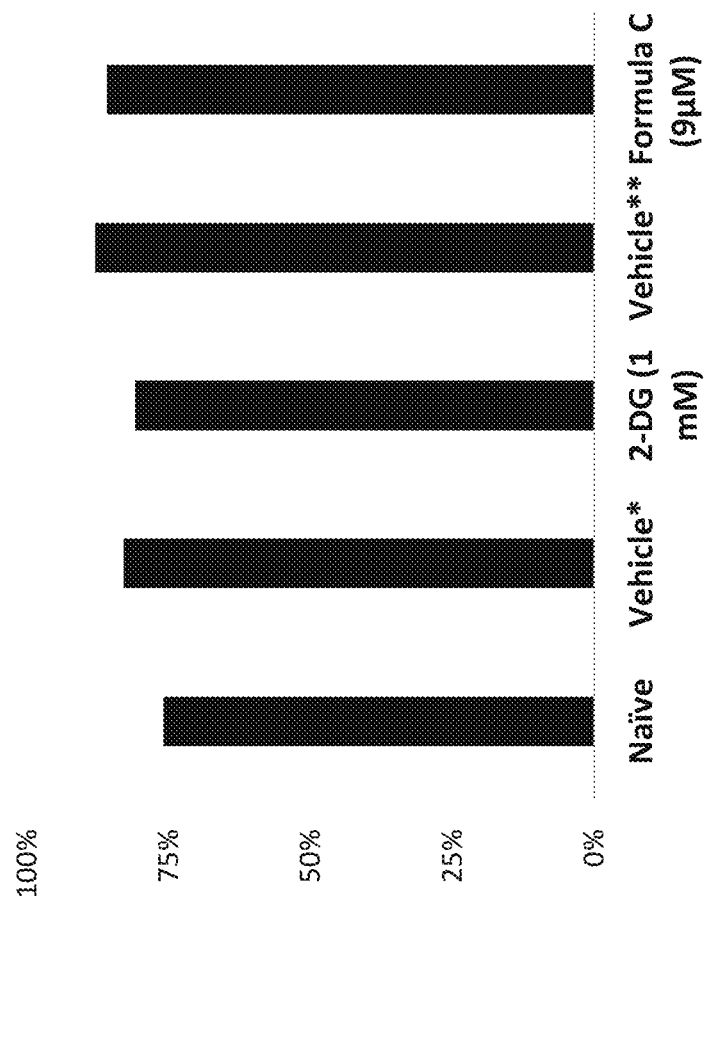

USE OF HEXOKINASE 2/MITOCHONDRIA-DETACHING COMPOUNDS FOR ACTIVATING IMMUNE RESPONSES

CROSS-REFERENCE TO RELATED APPLICATIONS

This application is a Continuation application of U.S. patent application Ser. No. 16/775,279 filed Nov. 26, 2017 which is a Divisional application of U.S. patent application Ser. No. 15/576,824 filed Nov. 26, 2017 which is a National Phase Application of PCT International Application No. PCT/IL2017/051213 filed Nov. 7, 2017, which claims priority to U.S. Provisional Application No. 62/418,323, filed Nov. 7, 2016, and to U.S. Provisional Application No. 62/573,179, filed Oct. 17, 2017, which are hereby incorporated by reference in their entirety.

FIELD OF THE INVENTION

The present invention provides methods of use of hexokinase 2 (HK2)/mitochondria-detaching compounds, including jasmonate derivatives and piperazine derivatives and pharmaceutical compositions including such compounds for potentiating immune responses in a subject, including potentiating immune responses in subjects with hyperproliferative disorders such as cancer and potentiating the immune response to infectious diseases.

BACKGROUND OF THE INVENTION

There is evidence to suggest the immune system may inhibit the development of cancer, via the innate immune system and/or the adaptive immune system, possibly via cancer-associated recognition events. The host may have a dedicated mechanism to perceive and eliminate transformed cells. In addition, adaptive immune recognition of tumor-associated and specific antigens also may be an important means by which the immune system controls the development of cancer. Furthermore, memory immune cells have an important role in anti-cancer immune-surveillance. Compounds that can induce an immune response in subjects with a hyperproliferative disorder are lacking.

SUMMARY OF THE INVENTION

In one embodiment, the present invention provides a compound that promotes the detachment of Hexokinase 2 (HK2) from the mitochondria for use in inducing an immune response in a subject.

In another embodiment, the present invention provides a compound that promotes the detachment of Hexokinase 2 (HK2) from the mitochondria for use in potentiating the immune response to a hyperproliferative disorder in a subject.

BRIEF DESCRIPTION OF THE DRAWINGS

FIGS. 7A-F. Formula C administration shifts effector CD8+ T cells to central memory cells. Primary Balb/C mouse splenocytes were grown in culture and activated by anti-CD3e and anti CD28 antibodies to shift them towards CD8+/CD4+ phenotype. Cells were then treated with Formula C (FIG. 7E), 2-DG (2-deoxyglucose, positive control) (FIG. 7C), or vehicle (FIG. 7B, FIG. 7D) for 24 hours followed by FACS analysis for CD44 and CD62L. FIG. 7A shows FACs analysis for CD44 and CD62L in non-activated splenoctyes. Formula C administration did not reduce the percentage of live cells in the sample (FIG. 7F).

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides a method of inducing an immune response in a subject comprising the step of contacting one or more cells of said subject with a therapeutically effective amount of a compound that promotes the detachment of Hexokinase 2 (HK2) from the mitochondria. In one embodiment, the compound is a jasmonate derivative. In another embodiment, the compound is a piperazine derivative.

In another embodiment, the present invention provides a method of activating an immune response in a subject comprising the step of contacting one or more cells of said subject with a therapeutically effective amount of a compound that promotes the detachment of Hexokinase 2 (HK2) from the mitochondria. In one embodiment, the compound is a jasmonate derivative. In another embodiment, the compound is a piperazine derivative.

In another embodiment, the present invention provides a method of potentiating an immune response in a subject comprising the step of contacting one or more cells of said subject with a therapeutically effective amount of a compound that promotes the detachment of Hexokinase 2 (HK2) from the mitochondria. In one embodiment, the compound is a jasmonate derivative. In another embodiment, the compound is a piperazine derivative.

In one embodiment, the compounds as described herein may be used to activate anti-cancer immune responses. In another embodiment, the compounds as described herein may be used to potentiate anti-cancer immune responses.

Figure 2:
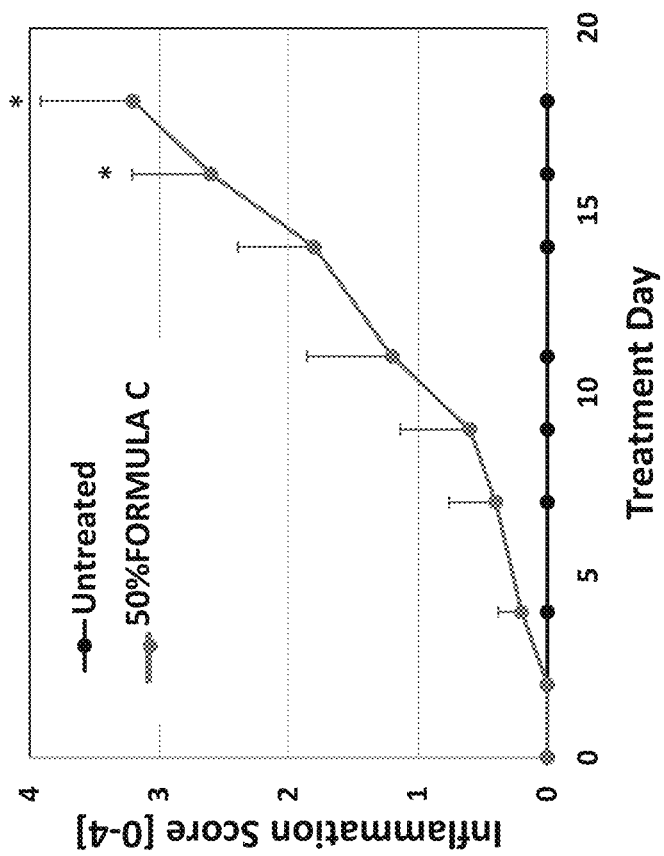
FIG. 2. Topical Formula C administration increases inflammation in the mouse B16-F10 melanoma model in the ear. * p≤0.05.
Figure 3B:
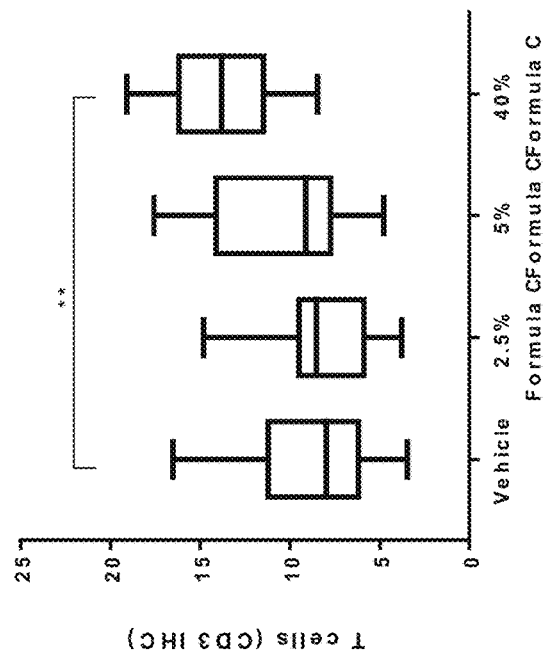
FIG. 3B. Box and Whiskers plot of semi-quantitative analysis of positive immunohistochemistry staining of skin sections stained with $CD3^+$ for T cells following 50-day of topical Formula C treatment of UVB-exposed mice. Quantification included the number of positive cells per ×40 high power field, 7 different fields per slide.
Figure 3C:
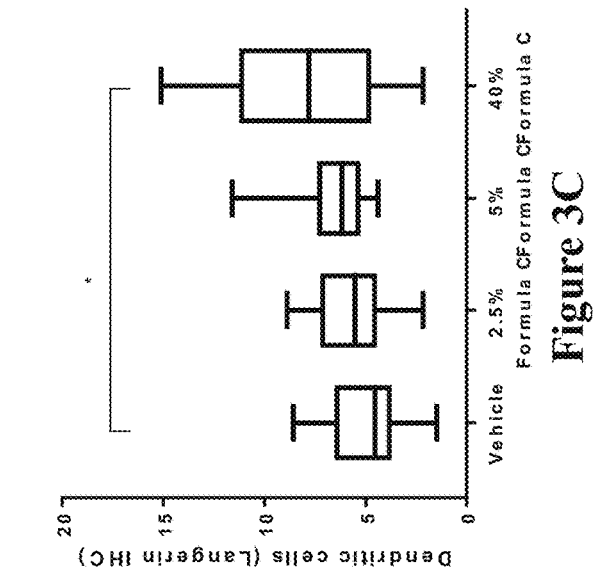
FIG. 3C. Box and Whiskers plot of semi-quantitative analysis of positive immunohistochemistry staining of skin sections stained with Langerin for skin dendritic cells following 50-day of topical Formula C treatment of UVB-exposed mice. Quantification included the number of positive cells per ×40 high power field, 7 different fields per slide.
Figure 3A:
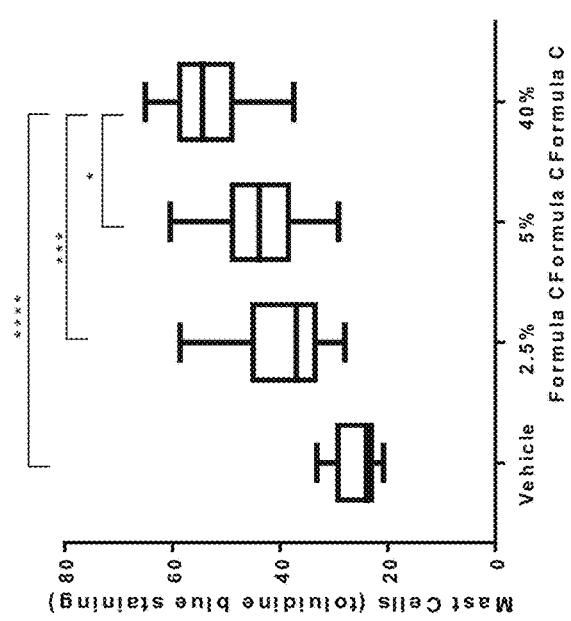
FIG. 3A. Box and Whiskers plot of semi-quantitative analysis of positive immunohistochemistry staining of skin sections stained with toluidine blue for mast cells following 50-day of topical Formula C treatment of UVB-exposed mice. Quantification included the number of positive cells per ×40 high power field, 7 different fields per slide.

Surprisingly and unexpectedly, the inventors have found that administration of the methyl jasmonate derivative Formula C leads to increased inflammatory response (FIG. 2) and the activation of an immune response in the skin of UVB-exposed mice model of actinic keratosis and squamous cell carcinoma (FIGS. 3A-C). Formula C administration also resulted in increased IL-1β secretion from macrophages (FIGS. 4 and 5A-D), and a shift of macrophages from the pro-tumor M2 phenotype to an anti-tumor M1 phenotype (FIGS. 6A-C). Finally, Formula C administration shifts T cells from effector T cells to memory T cells (FIGS. 7A-F).

Immune Responses

As used herein, the term "immune response" refers to any detectable response by the immune system of a host vertebrate animal, including, but not limited to, innate immune responses (e.g., activation of Toll receptor signaling cascade and stimulation of macrophages), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, stimulation of anti-tumor M1 macrophage phenotype, secretion of cytokines from macrophages, dendritic cell activation, T cell (e.g., CD4+ or CD8+ T cell) activation, induction of memory T cells, NK cell activation, B cell activation (e.g., antibody generation and/or secretion), mast cell activation, binding of an immunogen (e.g., antigen (e.g., immunogenic polypolypeptide)) to an MHC molecule, induction of a cytotoxic T lymphocyte ("CTL") response, induction of a B cell response (e.g., antibody production), and expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

In one embodiment, "inducing an immune response" may mean that an immune response was induced in a situation where there was no prior immune response. In another embodiment, an immune response is enhanced in a situation where there was some level of immune response before immune response induction. Thus, "inducing an immune response" includes "enhancing an immune response". In another embodiment, an inactive component of the immune system (e.g., macrophages or T cells) is activated in addition to other already activated components of the immune system. In another embodiment, the activity of an active component of the immune system (e.g., macrophages or T cells) is enhanced in addition to other already activated components of the immune system. In another embodiment, the activity of a component of the immune system (e.g., macrophages or T cells) is enhanced while the activity of another components of the immune system is decreased. Preferably, after inducing an immune response in a subject, said subject is protected from developing a disease or disorder such as cancer or the disease or disorder is ameliorated by inducing an immune response.

Thus, in one embodiment, the present invention provides a method of inducing a humoral immune response in a subject comprising the step of contacting one or more cells of said subject with a therapeutically effective amount of a HK2/mitochondria-detaching compound. In another embodiment, the present invention provides a method of inducing an innate immune response in a subject comprising the step of contacting one or more cells of said subject with a therapeutically effective amount of a HK2/mitochondria-detaching compound. In another embodiment, the present invention provides a method of inducing a cell-mediated immune response in a subject comprising the step of contacting one or more cells of said subject with a therapeutically effective amount of a HK2/mitochondria-detaching compound. In one embodiment, the HK2/mitochondria-detaching compound is a jasmonic acid derivative. In another embodiment, the HK2/mitochondria-detaching compound is a piperazine derivative.

Thus, in one embodiment, the present invention provides a method of activating a humoral immune response in a subject comprising the step of contacting one or more cells of said subject with a therapeutically effective amount of a HK2/mitochondria-detaching compound. In another embodiment, the present invention provides a method of activating an innate immune response in a subject comprising the step of contacting one or more cells of said subject with a therapeutically effective amount of a HK2/mitochondria-detaching compound. In another embodiment, the present invention provides a method of activating a cell-mediated immune response in a subject comprising the step of contacting one or more cells of said subject with a therapeutically effective amount of a HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

Thus, in one embodiment, potentiating a humoral immune response in a subject comprising the step of contacting one or more cells of said subject with a therapeutically effective amount of an HK2/mitochondria-detaching compound. In another embodiment, the present invention provides a method of potentiating an innate immune response in a subject comprising the step of contacting one or more cells of said subject with a therapeutically effective amount of an HK2/mitochondria-detaching compound. In another embodiment, the present invention provides a method of potentiating a cell-mediated immune response in a subject comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of activating T cells in a subject comprising the step of contacting one or more cells of said subject with a therapeutically effective amount of a HK2/mitochondria-detaching compound. In another embodiment, the T cell activation is enhanced T cell proliferation, enhanced cytokine production and/or enhanced T cell expression. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the term "T cell" refers to T lymphocytes as defined in the art and is intended to include thymocytes, immature T lymphocytes, mature T lymphocytes, resting T lymphocytes, or activated T lymphocytes. The T cells can be CD4+ T cells, CD8+ T cells, CD4+CD8+ T cells, or CD4−CD8− cells. The T cells can also be T helper cells, such as T helper 1 (TH1), or T helper 2 (TH2) cells, or TH17 cells, as well as cytotoxic T cells, regulatory T cells, natural killer T cells, naïve T cells, memory T cells, or gamma delta T cells.

In another embodiment, the present invention provides a method of reprogramming T cells to memory T cells. In another embodiment, the present invention provides a method of converting T cells to memory T cells. In another embodiment, the present invention provides a method of shifting T cells to memory T cells. In another embodiment, the present invention provides a method of increasing the number or percentage of memory T cells. In another embodiment, the present invention provides a method of increasing or expediting the effector to memory T cell transition.

In another embodiment, the present invention provides a method of increasing CD62L levels, CD44 levels, or a combination thereof in T cells, comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, memory T cells are central memory T cells ($T_{CM}$ cells). In another embodiment, memory T cells are effector memory T cells ($T_{EM}$ cells). In another embodiment, memory T cells are stem memory T cells ($T_{SCM}$ cells). In one embodiment, memory cells may be either CD4+ or CD8+.

In one embodiment, the methods as described herein are performed in vivo. In another embodiment, the methods are performed in vitro. In one embodiment, the methods are performed on primary cells. In one embodiment, the T cells can be from previously stored blood samples, from a healthy individual, or alternatively from an individual affected with a condition. In one embodiment, the condition is a hyperproliferative disease. In another embodiment, the condition is an infectious disease, such as a condition resulting from a viral infection, a bacterial infection or an infection by any other microorganism. In one embodiment, the T cells can be of human origin, murine origin or any other mammalian species.

In another embodiment, the present invention provides a method of converting macrophages from pro-tumor M2 to anti-tumor M1 phenotype comprising the step of contacting one or more cells of said subject with a therapeutically effective amount of a hexokinase 2 (HK2)/mitochondria-detaching compound. In another embodiment, the present invention provides a method of increasing MHCII levels, decreasing CD206 levels, or a combination thereof in a macrophage, comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, the present invention provides a method of stimulating secretion of cytokines from macrophages, comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative. In one embodiment, the cytokine comprises IL-1β, IL-18, or a combination thereof.

In another embodiment, the present invention provides a method of activating NK cells in a subject comprising the step of contacting one or more cells of said subject with a therapeutically effective amount of an HK2/mitochondria-detaching compound. In one embodiment, the NK cell activation is enhanced NK cell proliferation, enhanced cytokine production and/or enhanced NK cell expression. In another embodiment, the present invention provides a method of activating dendritic cells in a subject comprising the step of contacting one or more cells of said subject with a therapeutically effective amount of an HK2/mitochondria-detaching compound. In another embodiment, the dendritic cells activation is enhanced dendritic cells proliferation, enhanced cytokine production and/or enhanced dendritic cells expression. In another embodiment, the present invention provides a method of activating mast cells in a subject comprising the step of contacting one or more cells of said subject with a therapeutically effective amount of an HK2/mitochondria-detaching compound. In another embodiment, the mast cells activation is enhanced mast cells proliferation, enhanced cytokine production and/or enhanced mast cells expression. In another embodiment, the present invention provides a method of lowering the levels of myeloid-derived suppressor cells (MDSCs) comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of inducing inflammation in a subject comprising the step of contacting one or more cells of said subject with a therapeutically effective amount of an HK2/mitochondria-detaching compound. In one embodiment, the inflammation is acute inflammation. In another embodiment, the inflammation is chronic inflammation. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, the present invention provides a method of activating an inflammatory response in a subject comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, the present invention provides a method of activating an inflammasome in a subject comprising the step of contacting one or more cells of said subject with a therapeutically effective amount of an HK2/mitochondria-detaching compound. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, the present invention provides a method of inflammasome activation in a subject comprising the steps as described herein. In another embodiment, the present invention provides a method of inflammasome regulation in a subject comprising the steps as described herein. In another embodiment, the present invention provides a method of activating an inflammasome-mediated immune response in a subject comprising the steps as described herein.

Hexokinase 2 (HK2)/Mitochondria-Detaching Compounds

In one embodiment, compounds for use in the methods of the present invention comprise compounds that promote the detachment of HK2 from the mitochondria. In another embodiment, compounds for use in the methods of the present invention comprise compounds that promote the detachment of HK2 from VDAC (voltage-dependent anion channel). In another embodiment, compounds for use in the methods of the present invention comprise compounds that disrupt the physical contact between HK2 and the mitochondria in general or specifically between HK2 and VDAC.

In one embodiment, compounds that disrupt HK2/mitochondria attachment are known in the art. In another embodiment, compounds may be evaluated for such function by a skilled artisan. In one embodiment, disruption of HK2/mitochondria attachment may be assayed in a cell-free environment, using a technology such as microscale thermophoresis (MST), or others evaluating protein-protein interaction modulators (as described in U.S. Provisional Patent Application No. 62/577,256, which is incorporated by reference herein in its entirety). In another embodiment, disruption of HK2/mitochondria attachment may be assayed in a cell-based assay using various methods including, inter alia, Western blot, wherein the mitochondrial fraction is examined. Such methods are well known in the art.

In one embodiment, the compound comprises methyl jasmonate. In another embodiment, the compound comprises a methyl jasmonate derivative.

Jasmonate Derivatives

In one embodiment, the jasmonate derivative comprises a compound represented by the structure of Formula (VII):

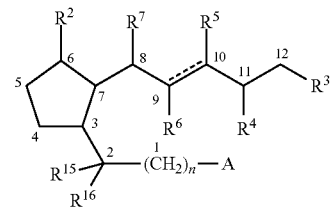

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof.

In a further embodiment, the compound is represented by the structure of formula C:

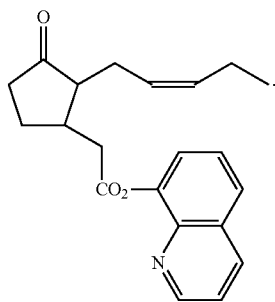

In one embodiment, the structure of formula C decouples HK2 from Voltage-dependent anion channel (VDAC) in cancer cells. In another embodiment, administration of an HK2/mitochondria-detaching compound to a cell leads to activation of an inflammasome in the cell. In another embodiment, administration of an HK2/mitochondria-detaching compound to a cell leads to an increase in one or more cytokines, which, in one embodiment, comprise IL-1β, and, in another embodiment, IL-18. In another embodiment, administration of an HK2/mitochondria-detaching compound to a cell leads to activation of an immune response in the cell. In one embodiment, the cell has high HK-2 expression. In one embodiment, the cell is a cancer cell. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, A is $COR^1$; $R^1$ is quinolinyloxy; $R^2$ is oxo; $R^3$, $R^4$, $R^5$, $R^6$ and $R^7$ are each hydrogen, wherein the bond between $C_9$ and $C_{10}$ can be a single or double bond; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof.

In another embodiment, the compound is represented by the structure of formula C:

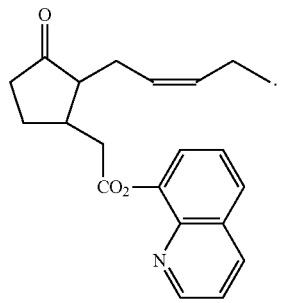

In one embodiment, ester derivatives of Jasmonic Acid may be used in the methods of the present invention. In another embodiment, other jasmonate derivatives may be used in the methods of the present invention. In one embodiment, halogenated jasmonate derivatives and related pharmaceutical compositions, as described in International Patent Application WO 2005/054172, which is incorporated by reference herein in its entirety, may be used in the methods of the present invention.

In another embodiment, jasmonate derivatives such as those described in International Patent Applications WO 2007/066336, WO 2010/143180, and WO 2007/066337, which are incorporated by reference herein in their entirety may be used in the methods of the present invention. In another embodiment, dermal compositions comprising jasmonate derivatives may be used in the methods of the present invention. Methods for preparing the jasmonate derivatives for use in the present invention are described, for example, in WO 2007/066336 and WO 2010/143180.

Piperazine Derivatives

In another embodiment, the compound for use in the present invention comprises piperazine derivatives, which in one embodiment, comprise the compounds described in PCT Application No. PCT/IL2017/050909, which is incorporated herein by reference in its entirety. According to this aspect and in one embodiment, the present invention provides the use of a compound represented by the structure of Formula (II):

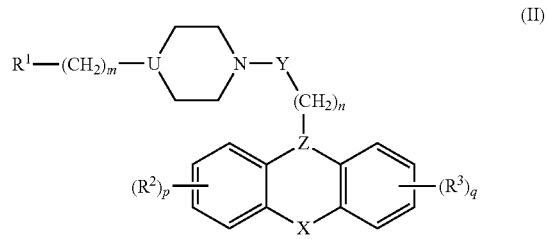

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof,
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2; and
p and q are each independently selected from 0, 1, 2, 3, and 4;
or a pharmaceutically acceptable salt thereof, with the proviso that when Z is CH, X is NH, S, or a bond.

In another embodiment, the following compound is excluded: a compound of Formula (II) wherein X is NH, Z is CH, Y is C=O, n is 0, m is 0, $R^1$ is a phenyl substituted by one or more alkoxy, and p and q are each 0.

In some embodiments, in the compound of Formula (II), m and n are each 0.

In some embodiments, in the compound of Formula (II), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (II), p is 0. In some embodiments, q is 0. In other embodiments, p is 0 and q is 0.

In some embodiments, in the compound of Formula (II), U is N.

In some embodiments, the compound for use in the invention is represented by a compound of Formula (III).

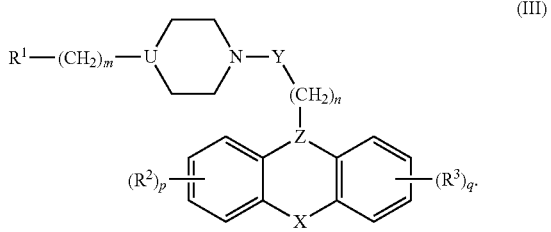

(III)

wherein X, U, $R^1$, $R^2$, $R^3$, m, n, p, and q are defined as anywhere herein.

In some embodiments, in the compound of Formula (III), X is O, NH, or a bond. In some embodiments, X is O. In other embodiments, X is a bond. In certain embodiments, X is NH.

In some embodiments, in the compound of Formula (III), m and n are each 0.

In some embodiments, in the compound of Formula (III), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (III), p is 0. In some embodiments, q is 0. In other embodiments, p is 0 and q is 0.

In some embodiments, in the compound of Formula (III), U is N.

In some embodiments, the compound for use in the present invention is represented by a compound of Formula (IV)

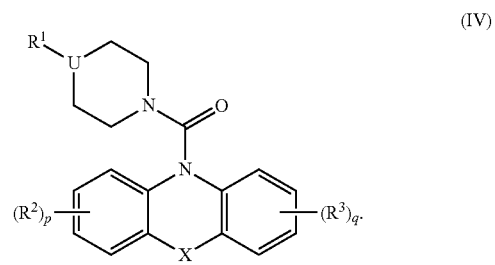

(IV)

wherein X, U, $R^1$, $R^2$, $R^3$, m, n, p, and q are defined as anywhere herein.

In some embodiments, in the compound of Formula (IV), X is O. In other embodiments, X is S. In certain embodiments, X is NH.

In some embodiments, in the compound of Formula (IV), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (IV), p is 0. In some embodiments, q is 0. In other embodiments, p is 0 and q is 0.

In some embodiments, in the compound of Formula (IV), U is N.

In some embodiments, the compound for use in the present invention is:

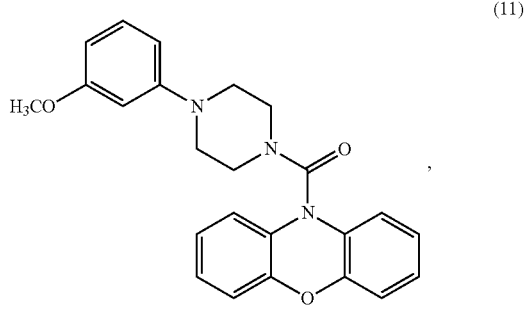

(11)

,

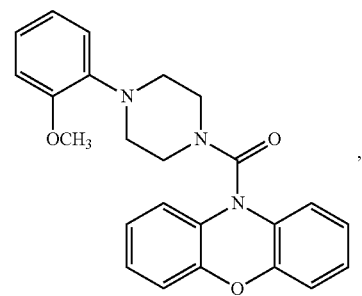
(12)
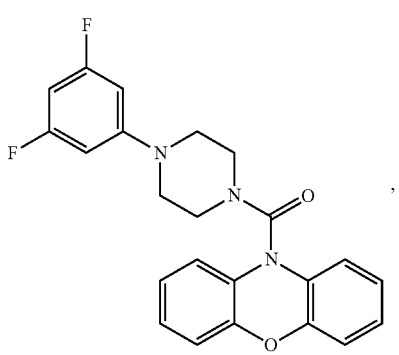
(13)
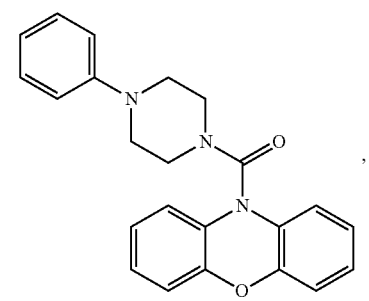
(1)
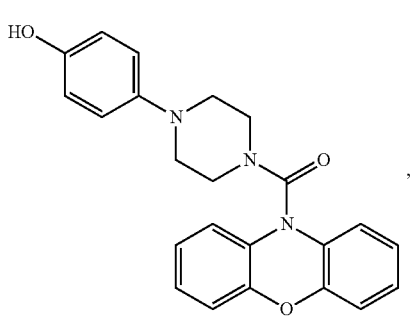
(14)
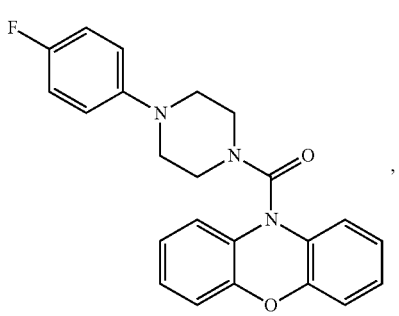
(15)
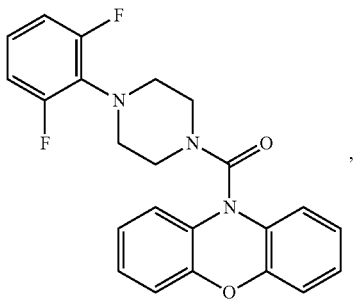
(5)
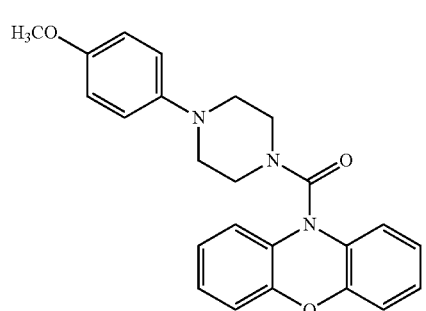
(4)
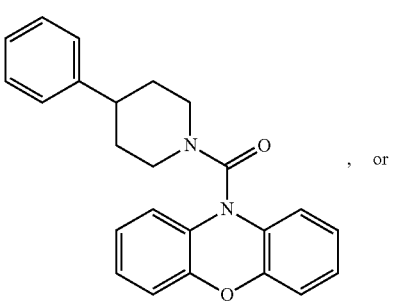
(16)
, or
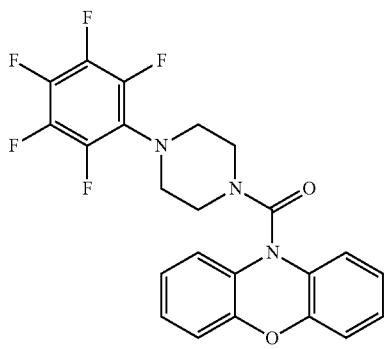
(2)
including salts, hydrates, solvates, polymorphs, optical isomers, geometrical isomers, enantiomers, diastereomers, and mixtures thereof.
In some embodiments, the compound for use in the invention is represented by a compound of Formula (V):

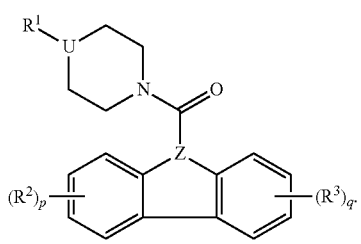

(V)

wherein X, U, $R^1$, $R^2$, $R^3$, m, n, p, and q are defined as anywhere herein.

In some embodiments, in the compound of Formula (V), Z is N. In other embodiments, Z is CH.

In some embodiments, in the compound of Formula (V), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof.

In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (V), p is 0. In some embodiments, q is 0. In other embodiments, p is 0 and q is 0.

In some embodiments, in the compound of Formula (V), U is N.

In some embodiments, the compound for use in the present invention is:

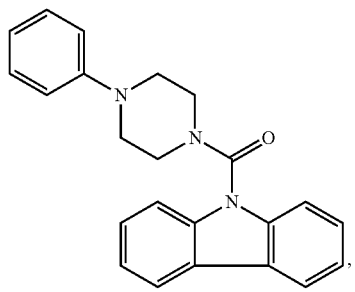

(20)

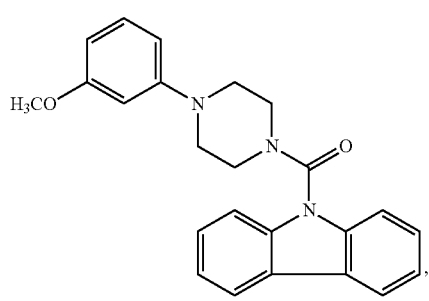

(21)

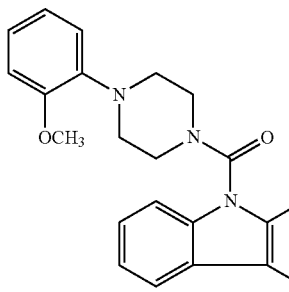

(22)

, or

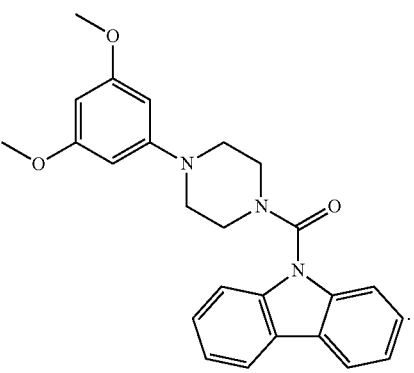

(23)

In some embodiments, the compound for use in the present invention comprises a di-meta-OMe analog, which in one embodiment is represented by a compound of Formula (24)

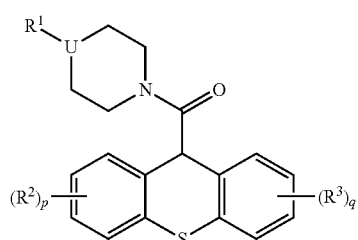

(24)

In some embodiments, the compound for use in the present invention is represented by a compound of Formula (VI):

(VI)

wherein U, $R^1$, $R^2$, $R^3$, p, and q are defined as anywhere herein.

In some embodiments, in the compound of Formula (VI), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (VI), p is 0. In some embodiments, q is 0. In other embodiments, p is 0 and q is 0.

In some embodiments, in the compound of Formula (VI), U is N.

In some embodiments, the compound for use in the present invention is:

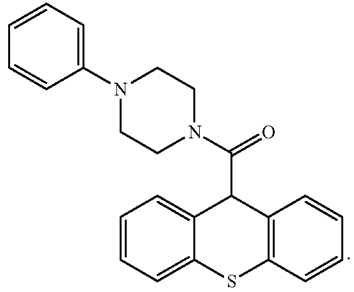

(3)

In another embodiment, $R^1$ is selected from the group consisting of phenyl, quinolinyl and isoquinolinyl, each of which may independently be unsubstituted or substituted with one or more halogen, $OR^a$ or $NR^aR^b$ wherein $R^a$ and $R^b$ are each independently selected from the group consisting of H or a $C_1$-$C_4$ alkyl.

In another embodiment, $R^1$ is C(=O)—$OR^a$ wherein $R^a$ is a $C_1$-$C_4$ alkyl. In other embodiments, $R^1$ is selected from the group consisting of:
a) phenyl;
b) fluorophenyl;
c) difluorophenyl;
d) pentafluorophenyl;
e) methoxyphenyl;
f)

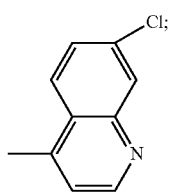

and
g) C(=O)—$OCH_2CH_3$.

Each possibility represents a separate embodiment of the present invention.

In some embodiments, in the compound of Formula (II) or in the compound of Formula (IV), X is S. In one embodiment, when X is S, Z is CH. In an alternative embodiment, the following compound is excluded: a compound of Formula (II) wherein X is S, Z is N, Y is C=O, n is 0, m is 0, $R^1$ is an unsubstituted or substituted phenyl and p and q are each 0. In another embodiment, the following compound is excluded: a compound of formula (II) wherein X is S, Z is N, Y is C=O, n is 0, m is 0, $R^1$ is pyridinyl and p and q are each 0.

In some embodiments wherein X is S, $R^1$ is aryl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is aryl substituted with one or more alkyl, arylalkyl, halogen, $NO_2$, CN, $OR^4$, and $NR^{5a}R^{5b}$, or a combination thereof. In some embodiments wherein X is S, $R^1$ is aryl substituted with one or more alkyl, arylalkyl, halogen, $NO_2$, and $NR^{5a}R^{5b}$, or a combination thereof. In some embodiments wherein X is S, $R^1$ is phenyl substituted with one or more alkyl, arylalkyl, halogen, $NO_2$, and $NR^{5a}R^{5b}$, or a combination thereof. In some embodiments wherein X is S, $R^1$ is aryl, optionally substituted with one or more halogen and $C_1$-$C_4$ alkyl, or a combination thereof. In some embodiments wherein X is S, $R^1$ is phenyl, optionally substituted with one or more halogen and $C_1$-$C_4$ alkyl, or a combination thereof.

In some embodiments wherein X is S, $R^1$ is heteroaryl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is not pyridinyl. In some embodiments wherein X is S, $R^1$ is heteroaryl substituted with one or more alkyl, arylalkyl, halogen, $NO_2$, CN, $OR^4$, and $NR^{5a}R^{5b}$, or a combination thereof. In some embodiments wherein X is S, $R^1$ is heteroaryl substituted with one or more alkyl, arylalkyl, halogen, $NO_2$, and $NR^{5a}R^{5b}$, or a combination thereof. In some embodiments wherein X is S, $R^1$ is quinolinyl, or isoquinolinyl. In some embodiments wherein X is S, $R^1$ is quinolinyl or isoquinolinyl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is quinolinyl or isoquinolinyl, optionally substituted with one or more halogen and $C_1$-$C_4$ alkyl, or a combination thereof. In certain embodiments wherein X is S, $R^1$ is C(=O)—$OR^a$, wherein $R^a$ is $C_1$-$C_4$ alkyl.

In one embodiment, the compound represented by the structure of Formula (II) as described herein is as described but having the proviso that:
(1) when Z is CH, X is NH, S, or a bond;
(2) when X is S, Z is CH; and
(3) the following compound: a compound of Formula (II) wherein X is NH, Z is CH, Y is C=O, n is 0, m is 0, $R^1$ is a phenyl substituted by one or more alkoxy, and p and q are each 0, is excluded.

In another embodiment, the compound represented by the structure of Formula (II) as described herein is as described but having the proviso that:
(1) when Z is CH, X is NH, S, or a bond and (2) the following compounds are excluded:
(i) a compound of Formula (II) wherein X is NH, Z is CH, Y is C=O, n is 0, m is 0, $R^1$ is a phenyl substituted by one or more alkoxy, and p and q are each 0; and
(ii) a compound of Formula (II) wherein X is S, Z is N, Y is C=O, n is 0, m is 0, $R^1$ is an unsubstituted or substituted phenyl and p and q are each 0.

In another embodiment, the compound represented by the structure of Formula (II) as described herein is as described but having the proviso that:
(1) when Z is CH, X is NH, S, or a bond;
(2) the following compounds are excluded:
(i) a compound of formula (II) wherein X is NH, Z is CH, Y is C=O, n is 0, m is 0, $R^1$ is a phenyl substituted by one or more alkoxy, and p and q are each 0; and (ii) a compound of formula (II) wherein X is S, Z is N, Y is C═O, n is 0, m is 0, R¹ is pyridinyl and p and q are each 0.

In one embodiment, the compound is represented by Formula (II), wherein n is 0. According to this aspect and in one embodiment, the compound is represented by the structure of Formula (II-a):

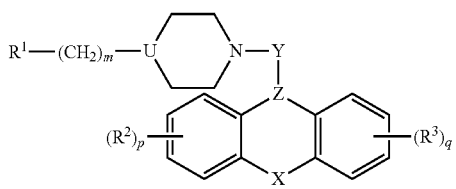

(II-a)

In another embodiment, the compound is represented by Formula (II) wherein X is O, Z is N, Y is C═O, n is 0, m is 0, R¹ is phenyl or methoxyphenyl and p and q are each 0.

In yet another embodiment, the compound is represented by Formula (II) wherein X is S, Z is CH, Y is C═O, n is 0, m is 0, R¹ is phenyl and p and q are each 0.

In one embodiment, the compound is represented by Formula (II) wherein X is O, Z is N, Y is C═O, n is 0, m is 0, R¹ is methoxyphenyl and p and q are each 0. In another embodiment, the compound is represented by Formula (II), wherein X is O, Z is N, Y is C═O, n is 0, m is 0, R¹ is difluorophenyl or pentafluorophenyl and p and q are each 0.

In another embodiment the compound is represented by Formula (II), wherein p and q are each 0 (i.e., R² and R³ do not exist).

As demonstrated herein, said compound has unexpectedly been found to be a highly potent and selective cytotoxic agent, exhibiting selective cytotoxicity towards cancer as well as pre-cancerous cells and benign hyperproliferative disorders, while having little effect on normal cells.

As used herein, in some embodiments, an "alkyl" group refers to any saturated aliphatic hydrocarbon, including straight-chain and branched-chain alkyl groups. In one embodiment, the alkyl group has 1-4 carbons designated here as $C_1$-$C_4$-alkyl. In some embodiments, the alkyl group has 1-7 carbons designated here as $C_1$-$C_7$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl contains 5 or more ring atoms. In some embodiments, the heteroaryl group contains 5-10 ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, quinolyl (e.g. 1-quinolinyl, 2-quinolinyl, 3-quinolinyl, 4-quinolinyl, 5-quinolinyl, 6-quinolinyl, 7-quinolinyl and 8-quinolinyl), isoquinolinyl (e.g., 1-isoquinolinyl, 2-isoquinolinyl, 3-isoquinolinyl, 4-isoquinolinyl, 5-isoquinolinyl, 6-isoquinolinyl, 7-isoquinolinyl and 8-isoquinolinyl); naphthyridinyl (e.g., 1-naphthyridinyl, 2-naphthyridinyl), quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The term "halogen" or "halo" as used herein alone or as part of another group refers to chlorine, bromine, fluorine, and iodine.

The term "hydroxy" refers to an OH group. The terms "alkoxy" refers to the group $OR^a$ wherein $R^a$ is a $C_1$-$C_4$ alkyl as defined above. Nonlimiting examples of an alkoxy group is methoxy, ethoxy, n-propoxy, isopropoxy, n-butoxy, t-butoxy and like groups.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. The present invention intends to encompass all structural and geometrical isomers including cis, trans, E and Z isomers.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counter-ions for the anion of a salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylene diammonium, and like cations. See, for example, "Pharmaceutical Salts," Berge et al., J. Pharm. Sci., 66:1-19 (1977), which is incorporated herein by reference.

The present invention also includes the use of solvates of the compounds of the present invention and salts thereof "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes use of polymorphs of the compounds of the present invention and salts thereof. The term "polymorph" refers to a particular crystalline state of a substance, which can be characterized by particular physical properties such as X-ray diffraction, IR spectra, melting point, and the like.

Other Compounds

In another embodiment, the compound for use in the present invention comprises 2-deoxyglucose (2-DG). In one embodiment, the compound comprises a peptide derived from the N-terminus of HK2, which in one embodiment, is HKVBD. Such peptides derived from the N-terminus of HK2 are known in the art and described, for example, in Wolf et al. 2016 (Cell. 2016 Jul. 28; 166(3):624-636) and Pastorino et al 2002 (JBC 277:7610-8), which are incorporated by reference herein in their entirety. In another embodiment, the compound comprises a peptidoglycan, which in one embodiment, is a bacterial peptidoglycan. In another embodiment, the compound comprises N-acetylglucosamine. In another embodiment, the compound comprises glucose-6-phosphate (G6P). In another embodiment, the compound comprises Lonidamine. In another embodiment, the compound comprises 3-bromopyruvate. In another embodiment, the compound comprises clotrimazole. In another embodiment, the compound comprises shRNA, which in one embodiment, comprises VDAC shRNA and, in another embodiment, comprises HK2 shRNA.

Inflammasomes

In one embodiment, the inflammasome is a cellular protein complex that triggers secretion of one or more cytokines, which, in one embodiment, activates or recruits the immune system.

In one embodiment, the inflammasome is a multiprotein oligomer consisting of caspase 1, PYCARD, NALP and sometimes caspase 5 (also known as caspase 11 or ICH-3). It is expressed in myeloid cells and is a component of the innate immune system.

In one embodiment, the inflammasome as described herein is an NLRP inflammasome. In one embodiment, the NLRP inflammasome is an NLRP3 inflammasome. In another embodiment, the inflammasome is NLRP1 inflammasome. In one embodiment, the inflammasome is an NLRC inflammasome. In one embodiment, the NLRC inflammasome is an NLRC4 inflammasome.

In one embodiment, the activation of said inflammasome increases processing and/or secretion of interleukin (IL)-1β. In another embodiment, the activation of said inflammasome increases processing and/or secretion of IL-18.

In another embodiment, administration of the compounds of the present invention increases Caspase-1 activation.

Cancer and Tumors

In one embodiment, the present invention provides a method of treating a solid tumor or hematological malignancy in a subject by inducing an immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating an immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by potentiating an immune response in a subject comprising the step of contacting one or more cells of said subject with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of treating a solid tumor or hematological malignancy in a subject by inducing an innate immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating an innate immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by potentiating an innate immune response in a subject comprising the step of contacting one or more cells of said subject with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of treating a solid tumor or hematological malignancy in a subject by inducing a humoral immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating a humoral immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by potentiating a humoral immune response in a subject comprising the step of contacting one or more cells of said subject with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of treating a solid tumor or hematological malignancy in a subject by inducing a cell-mediated immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating a cell-mediated immune response in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by potentiating a cell-mediated immune response in a subject comprising the step of contacting one or more cells of said subject with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, the present invention provides a method of treating a solid tumor or hematological malignancy in a subject by activating T cells in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating NK cells in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating dendritic cells in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating mast cells in a subject comprising the step of contacting one or more cells of said subject with a therapeutically effective amount of an HK2/mitochondria-detaching compound, as described herein. In another embodiment, the present invention provides a method of treating a solid tumor or hematological malignancy in a subject by activating dendritic cells in a subject comprising the step of contacting one or more cells of said subject with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In another embodiment, the present invention provides a method of treating a solid tumor or hematological malignancy in a subject by increasing inflammation in situ, the method comprising contacting solid tumor or hematological malignancy cells with a therapeutically effective amount of an HK2/mitochondria-detaching compound, as described herein. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In still another embodiment, the administration of the compound as described herein reduces growth of the cells of the solid tumor or hematological malignancy by 40%, 50%, 60%, 70%, 80%, 90% or 95% compared to growth of the cells of the solid tumor or hematological malignancy that have not been treated with the compound.

In one embodiment, the cells contacted with the compound as described herein are abnormal. In one embodiment, the cells are cancerous.

In one embodiment, a subject as described herein has cancer. In one embodiment, the term "cancer" in the context of the present invention includes all types of neoplasm whether in the form of solid or non-solid tumors, and includes both malignant and premalignant conditions as well as their metastasis.

In one embodiment, a subject as described herein has a pre-cancerous condition. In another embodiment, a subject as described herein has a benign hyperproliferative disorder. In another embodiment, said subject has cancer.

In one embodiment, the term "pre-cancer" or "pre-malignant" as used herein interchangeably refers to diseases, syndromes or other conditions associated with an increased risk of cancer. Pre-cancer conditions in the context of the present invention include, but are not limited to: breast calcifications, vaginal intra-epithelial neoplasia, Barrett's esophagus, atrophic gastritis, dyskeratosis congenital, sideropenic dysphagia, lichen planus, oral sibmucous fibrosis, actinic keratosis, solar elastosis, cervical desplasia, leukoplakia and erythroplakia.

In one embodiment, the term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting examples of benign hyperproliferative disorder are psoriasis and benign prostatic hyperplasia (BPH).

In one embodiment, the cancer is a carcinoma, sarcoma, myeloma, leukemia, or lymphoma. In another embodiment, the cancer is a mixed type.

In one embodiment, the carcinoma is an adenocarcinoma. In another embodiment, the carcinoma is a squamous cell carcinoma.

In one embodiment, the sarcoma comprises osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); and Mesenchymous or mixed mesodermal tumor (mixed connective tissue types).

In one embodiment, the subject has a myeloma, which, in one embodiment, is cancer that originates in the plasma cells of bone marrow. The plasma cells produce some of the proteins found in blood.

In another embodiment, the subject has a leukemia ("non-solid tumor" or "blood cancer"), which in one embodiment, is a cancer of the bone marrow (the site of blood cell production). In one embodiment, leukemia comprises myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); and Polycythemia vera or erythremia (malignancy of various blood cell products, but with red cells predominating).

In another embodiment, the subject has a lymphoma. In one embodiment, lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias, which are sometimes called "non-solid tumors," lymphomas are "solid cancers." Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Mixed Type cancers contain several types of cells. The type components may be within one category or from different categories. Some examples are: adenosquamous carcinoma; mixed mesodermal tumor; carcinosarcoma; teratocarcinoma As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, lung cancer, bone cancer, liver cancer, stomach cancer, bladder cancer, colon cancer, colorectal cancer, pancreatic cancer, cancer of the thyroid, head and neck cancer, cancer of the central nervous system, brain cancer, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

In one embodiment, a subject as described herein has been diagnosed with a lymphoma. In one embodiment, the lymphoma is a cutaneous T-cell lymphoma (CTCL). In one embodiment, CTCL occurs when T cells become cancerous. In one embodiment, CTCL affect the skin, causing different types of skin lesions.

In one embodiment, the CTCL is Mycosis fungoides. In one embodiment, Mycosis fungoides or Alibert-Bazin syndrome or granuloma fungoides, is the most common form of cutaneous T-cell lymphoma. In one embodiment, Mycosis fungoides generally affects the skin, but may progress internally over time. In another embodiment, the CTCL is Sézary syndrome. In one embodiment, Sézary syndrome is an aggressive form of CTCL.

Thus, in one embodiment, the cancer is a skin tumor.

In one embodiment, the skin tumor is a benign hyperproliferative skin lesion, a pre-cancerous tumor or a cancerous tumor.

In one embodiment, the benign hyperproliferative skin lesion is psoriasis. In another embodiment, the benign hyperproliferative skin lesion is Ledderhose Disease, Dupuytren's Disease, a keloid or a hypertrophic scar.

In one embodiment, the pre-cancerous tumor is actinic keratosis. In a further embodiment, the pre-cancerous tumor is Bowen's Disease.

In one embodiment, the cancerous tumor is a melanoma. In another embodiment, the cancerous tumor is a basal cell carcinoma, a squamous cell carcinoma or a cutaneous T-cell lymphoma.

In one embodiment, the cutaneous T-cell lymphoma is mycosis fungoides or Sézary syndrome.

In one embodiment, the cancer comprises a solid tumor.

In one embodiment, the solid tumor comprises stomach cancer, colon cancer, kidney cancer, pancreatic cancer, thyroid cancer, head and neck cancer, or a combination thereof.

In another embodiment, the cancer comprises prostate cancer. In one embodiment, prostate cancer comprises castration resistant prostate cancer (CRPC), which, in one embodiment, comprises metastatic castration resistant prostate cancer (mCRPC).

In another embodiment, the cancer comprises breast cancer. In one embodiment, breast cancer comprises triple negative breast cancer (TNBC).

In one embodiment, the solid tumor comprises lung cancer.

In one embodiment, the lung cancer comprises small cell lung carcinoma, non-small cell lung carcinoma, or large cell lung carcinoma.

In one embodiment, the solid tumor comprises melanoma.

In one embodiment, the cancer comprises squamous cell carcinoma (SCC), basal cell carcinoma, or a combination thereof.

In another embodiment, the cancer is an adenocarcinoma of the stomach or gastroesophageal junction, Dermatofibrosarcoma protuberans, Endocrine/neuroendocrine tumors, Gastrointestinal stromal tumor, Giant cell tumor of the bone, Kaposi sarcoma, Myelodysplastic/myeloproliferative disorders, Ovarian epithelial/fallopian tube/primary peritoneal cancers, Soft tissue sarcoma, Systemic mastocytosis, Germ cell tumor, or a combination thereof.

In one embodiment, the cancer comprises a hematological malignancy.

In one embodiment, the hematological malignancy comprises leukemia.

In one embodiment, the leukemia comprises lymphoblastic leukemia, which, in one embodiment comprises acute lymphoblastic leukemia (ALL), acute myeloid leukemia (AML), chronic lymphocytic leukemia (CLL), and chronic myeloid leukemia (CML).

In another embodiment, the hematological malignancy comprises a lymphoma, which in one embodiment is Non-Hodgkin lymphoma.

Additional Therapeutic Agents

In another embodiment, any of the methods of the present invention further comprise the step of contacting one or more cells of said subject with a therapeutic agent, which in one embodiment, comprises an anti-cancer drug.

In one embodiment, the anti-cancer drug comprises a chemotherapeutic agent.

In one embodiment, the chemotherapeutic agent comprises Imiquimod, 5-Fluorouracil (5-FU), diclofenac, ingenol mebutate, or a combination thereof.

In another embodiment, the chemotherapeutic agent comprises Bleomycin, capecitabine, cisplatin, Cyclophosphamide, dacarbazine, Doxorubicin, Epirubicin, etoposide, folinic acid, Methotrexate, Mustine, oxaliplatin, prednisolone, procarbazine, vinblastine, vincristine, or a combination thereof.

In another embodiment, the provided methods further comprise removal of the skin tumor by Mohs surgery.

Targeted Therapies

In another embodiment, the present invention provides a method as described herein comprising contacting one or more cells of said subject with a compound as described herein and a targeted therapy.

In one embodiment, the present invention provides methods of treating cancer comprising administering a compound as described herein in combination with one or more targeted therapies.

In one embodiment, the immunotherapeutic compound is targeted to particular molecules expressed abnormally by cancer cells. In one embodiment, the targeted therapy comprises a hormone therapy, signal transduction inhibitor, gene expression modulator, apoptosis inducer, angiogenesis inhibitor, immunotherapy, or toxin delivery molecules.

In one embodiment, the targeted therapy utilizes small molecules. In another embodiment, the targeted therapy utilizes antibodies, which, in one embodiment, are monoclonal antibodies.

In one embodiment, the immunotherapeutic compound comprises abiraterone acetate (Zytiga®), ado-trastuzumab emtansine (Kadcyla®), afatinib dimaleate (Gilotrif®), alectinib (Alecensa®), alemtuzumab (Campath®), Alitretinoin (Panretin®), anastrozole (Arimidex®), Atezolizumab (Tecentriq™), axitinib (Inlyta®), belinostat (Beleodaq®), Bevacizumab (Avastin®), bexarotene (Targretin®), blinatumomab (Blincyto®), bortezomib (Velcade®), bosutinib (Bosulif®), brentuximab vedotin (Adcetris®), Cabazitaxel (Jevtana®), cabozantinib (Cabometyx™), Cabozantinib (Cometriq®), carfilzomib (Kyprolis®), ceritinib (LDK378/Zykadia™), Cetuximab (Erbitux®), cobimetinib (Cotellic™), crizotinib (Xalkori®), dabrafenib (Tafinlar®), daratumumab (Darzalex™), dasatinib (Sprycel®), denileukin diftitox (Ontak®), Denosumab (Xgeva®), Dinutuximab (Unituxin™), elotuzumab (Empliciti™) enzalutamide (Xtandi®), Erlotinib (Tarceva®), everolimus (Afinitor®), exemestane (Aromasin®), fulvestrant (Faslodex®), gefitinib (Iressa®), Ibritumomab tiuxetan (Zevalin®), ibrutinib (Imbruvica®), idelalisib (Zydelig®), Imatinib mesylate (Gleevec®), Ipilimumab (Yervoy®), ixazomib citrate (Ninlaro®), Lanreotide acetate (Somatuline® Depot), lapatinib (Tykerb®), lenvatinib mesylate (Lenvima®), letrozole (Femara®), necitumumab (Portrazza™) nilotinib (Tasigna®), nivolumab (Opdivo®), obinutuzumab (Gazyva®), ofatumumab (Arzerra®), olaparib (Lynparza™), olaratumab (Lartruvo™), osimertinib (Tagrisso™) palbociclib (Ibrance®), panitumumab (Vectibix®), panobinostat (Farydak®), pazopanib (Votrient®), pembrolizumab (Keytruda®), pertuzumab (Perjeta®), pralatrexate (Folotyn®), radium 223 dichloride (Xofigo®), ramucirumab (Cyramza®), regorafenib (Stivarga®), rituximab (Rituxan®), romidepsin (Istodax®), ruxolitinib phosphate (Jakafi®), siltuximab (Sylvant®), sonidegib (Odomzo®), sorafenib (Nexavar®), sunitinib (Sutent®), tamoxifen (Nolvadex), temsirolimus (Torisel®), toremifene (Fareston®), trametinib (Mekinist®), Trastuzumab (Herceptin®), Tretinoin (Vesanoid®), vandetanib (Caprelsa®), vemurafenib (Zelboraf®), venetoclax (Venclexta™), Vismodegib (Erivedge®), vorinostat (Zolinza®), ziv-aflibercept (Zaltrap®), or a combination thereof.

In another embodiment, methods of the present invention further comprise the step of contacting one or more cells of the subject with an immunotherapeutic compound.

Immunotherapeutic Compounds

In one embodiment, an immunotherapy as described herein is a monoclonal antibody that recognizes specific molecules on the surface of cancer cells. In one embodiment, binding of the monoclonal antibody to the target molecule results in the immune destruction of cells that express that target molecule. In another embodiment, the antibody binds to certain immune cells to enhance their actions on cancer cells.

In one embodiment, the immunotherapeutic compound comprises imatinib or trastuzumab.

In one embodiment, the immunotherapeutic compound comprises a checkpoint inhibitor.

In one embodiment, the checkpoint inhibitor comprises a Programmed cell Death protein 1 (PD1) inhibitor or a Programmed cell Death Ligand 1 (PD-L1) inhibitor.

In one embodiment, the PD-1 or PD-L1 inhibitor is an antibody.

In one embodiment, the antibody comprises Nivolumab, Pembrolizumab, Pidilizumab, Avelumab, BMS 936559, or MPDL328OA.

Chimeric Antigen Receptor-Expressing T-Cells (CAR T-Cells)

In one embodiment, the immunotherapeutic compound comprises chimeric antigen receptor T cells (CAR T-cells).

In another embodiment, an immunotherapy as described herein is adoptive cell transfer (ACT) therapy. In one embodiment, ACT therapy comprises cytotoxic T-cells from a patient or donor that are engineered to express a chimeric antigen receptor (CAR T-cells) targeted to a tumor specific antigen expressed on the surface of the tumor cells. These CAR T-cells are then cytotoxic only to cells expressing the tumor specific antigen.

In one embodiment, chimeric antigen receptors (CARs) are a type of antigen-targeted receptor composed of intracellular T-cell signaling domains fused to extracellular tumor-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients. Initial CARs fused antigen-recognition domains to the CD3ζ activation chain of the T-cell receptor (TCR) complex. While these first generation CARs induced T-cell effector function in vitro, they were largely limited by poor antitumor efficacy in vivo. Subsequent CAR iterations have included secondary costimulatory signals in tandem with CD3ζ, including intracellular domains from CD28 or a variety of TNF receptor family molecules such as 4-1BB (CD137) and OX40 (CD134). Further, third generation receptors include two costimulatory signals in addition to CD3ζ, most commonly from CD28 and 4-1BB. Second and third generation CARs dramatically improved antitumor efficacy, in some cases inducing complete remissions in patients with advanced cancer.

In one embodiment, a CAR T-cell is an immunoresponsive cell comprising an antigen receptor, which is activated when its receptor binds to its antigen.

In one embodiment, the CAR T-cells used in the compositions and methods as disclosed herein are first generation CAR T-cells. In another embodiment, the CAR T-cells used in the compositions and methods as disclosed herein are second generation CAR T-cells. In another embodiment, the CAR T-cells used in the compositions and methods as disclosed herein are third generation CAR T-cells. In another embodiment, the CAR T-cells used in the compositions and methods as disclosed herein are fourth generation CAR T-cells.

In one embodiment, first-generation CARs have one signaling domain, typically the cytoplasmic signaling domain of the CD3 TCRζ chain.

In another embodiment, the CAR T-cells as disclosed herein are second generation CAR T-cells. In another embodiment, CAR T-cells as disclosed herein comprise a tripartite chimeric receptor (TPCR). In one embodiment, CAR T-cells as disclosed herein, comprise one or more signaling moieties that activate naïve T-cells in a co-stimulation independent manner. In another embodiment, the CAR T-cells further encode one or more members of the tumor necrosis factor receptor family, which in one embodiment, is CD27, 4-1BB (CD137), or OX40 (CD134), or a combination thereof.

Third-generation CAR T-cells attempt to harness the signaling potential of 2 costimulatory domains: in one embodiment, the CD28 domain followed by either the 4-1BB or OX-40 signaling domains. In another embodiment, the CAR T-cells used in the compositions and methods as disclosed herein further encode a co-stimulatory signaling domain, which in one embodiment is CD28. In another embodiment, the signaling domain is the CD3ζ-chain, CD97, GDI la-CD18, CD2, ICOS, CD27, CD154, CDS, OX40, 4-1BB, CD28 signaling domain, or combinations thereof.

In one embodiment, telomere length and replicative capacity correlate with the engraftment efficiency and anti-tumor efficacy of adoptively transferred T-cell lines. In one embodiment, CD28 stimulation maintains telomere length in T-cells.

In one embodiment, CAR-modified T-cell potency may be further enhanced through the introduction of additional genes, including those encoding proliferative cytokines (ie, IL-12) or costimulatory ligands (ie, 4-1BBL), thus producing "armored" fourth-generation CAR-modified T-cells. In one embodiment, "armored CAR T-cells," are CAR T-cells which are protected from the inhibitory tumor microenvironment. In another embodiment, the "armored" CAR technology incorporates the local secretion of soluble signaling proteins to amplify the immune response within the tumor microenvironment with the goal of minimizing systemic side effects. In one embodiment, the signaling protein signal is IL-12, which can stimulate T-cell activation and recruitment. In one embodiment, "armored" CAR technology is especially useful in solid tumor indications, in which microenvironment and potent immunosuppressive mechanisms have the potential to make the establishment of a robust anti-tumor response more challenging.

In one embodiment, CAR T-cells are genetically modified to encode molecules involved in the prevention of apoptosis, the remodeling of the tumor microenvironment, induction of homeostatic proliferation, and chemokine receptors that promote directed T-cell homing.

In one embodiment, the CAR binds to an epitope of an antigen via an antibody or an antibody fragment that is directed to the antigen. In another embodiment, the antibody is a monoclonal antibody. In another embodiment, the antibody is a polyclonal antibody. In another embodiment, the antibody fragment is a single-chain variable fragment (scFv).

In another embodiment, the CAR T-cells of the compositions as disclosed herein bind to a tumor associated antigen (TAA). In another embodiment, said tumor associated antigen is: Mucin 1, cell surface associated (MUC1) or polymorphic epithelial mucin (PEM), Arginine-rich, mutated in early stage tumors (Armet), Heat Shock Protein 60 (HSP60), calnexin (CANX), methylenetetrahydrofolate dehydrogenase (NADP+ dependent) 2, methenyltetrahydrofolate cyclohydrolase (MTHFD2), fibroblast activation protein (FAP), matrix metallopeptidase (MMP6), B Melanoma Antigen-1 (BAGE-1), aberrant transcript of N-acetyl glucosaminyl transferase V (GnTV), Q5H943, Carcinoembryonic antigen (CEA), Pmel, Kallikrein-4, Mammaglobin-1, MART-1, GPR143-OA1, prostate specific antigen (PSA), TRP1, Tyrosinase, FGP-5, NEU proto-oncogene, Aft, MMP-2, prostate specific membrane antigen (PSMA), Telomerase-associated protein-2, Prostatic acid phosphatase (PAP), Uroplakin II or Proteinase 3.

In another embodiment, the CAR binds to CD19 or CD20 to target B cells in the case where one would like to destroy B cells as in leukemia. In another embodiment, the CAR binds to ROR1, CD22, or GD2. In another embodiment, the CAR binds to NY-ESO-1. In another embodiment, the CAR binds to MAGE family proteins. In another embodiment, the CAR binds to mesothelin. In another embodiment, the CAR binds to c-erbB2. In another embodiment, the CAR binds to mutational antigens that are tumor specific, such as BRAFV600E mutations and BCR-ABL translocations. In another embodiment, the CAR binds to viral antigens which are tumor-specific, such as EBV in HD, HPV in cervical cancer, and polyomavirus in Merkel cancer. In another embodiment, the CAR T-cell binds to Her2/neu. In another embodiment, the CAR T-cell binds to EGFRvIII.

In one embodiment, the chimeric antigen receptor (CAR) T-cell binds the CD19 antigen. In another embodiment, the CAR binds the CD22 antigen. In another embodiment, the CAR binds to alpha folate receptor. In another embodiment, the CAR binds to CAIX. In another embodiment, the CAR binds to CD20. In another embodiment, the CAR binds to CD23. In another embodiment, the CAR binds to CD24. In another embodiment, the CAR binds to CD30. In another embodiment, the CAR binds to CD33. In another embodiment, the CAR binds to CD38. In another embodiment, the CAR binds to CD44v6. In another embodiment, the CAR binds to CD44v7/8. In another embodiment, the CAR binds to CD123. In another embodiment, the CAR binds to CD171. In another embodiment, the CAR binds to carcinoembryonic antigen (CEA). In another embodiment, the CAR binds to EGFRvIII. In another embodiment, the CAR binds to EGP-2. In another embodiment, the CAR binds to EGP-40. In another embodiment, the CAR binds to EphA2. In another embodiment, the CAR binds to Erb-B2. In another embodiment, the CAR binds to Erb-B 2,3,4. In another embodiment, the CAR binds to Erb-B3/4. In another embodiment, the CAR binds to FBP. In another embodiment, the CAR binds to fetal acetylcholine receptor. In another embodiment, the CAR binds to $G_{D2}$. In another embodiment, the CAR binds to $G_{D3}$. In another embodiment, the CAR binds to HER2. In another embodiment, the CAR binds to HMW-MAA. In another embodiment, the CAR binds to IL-11 Ralpha. In another embodiment, the CAR binds to IL-13Ralpha1. In another embodiment, the CAR binds to KDR. In another embodiment, the CAR binds to kappa-light chain. In another embodiment, the CAR binds to Lewis Y. In another embodiment, the CAR binds to L1-cell adhesion molecule. In another embodiment, the CAR binds to MAGE-A1. In another embodiment, the CAR binds to mesothelin. In another embodiment, the CAR binds to CMV infected cells. In another embodiment, the CAR binds to MUC1. In another embodiment, the CAR binds to MUC16. In another embodiment, the CAR binds to NKG2D ligands. In another embodiment, the CAR binds to NY-ESO-1 (amino acids 157-165). In another embodiment, the CAR binds to oncofetal antigen (h5T4). In another embodiment, the CAR binds to PSCA. In another embodiment, the CAR binds to PSMA. In another embodiment, the CAR binds to ROR1. In another embodiment, the CAR binds to TAG-72. In another embodiment, the CAR binds to VEGF-R2 or other VEGF receptors. In another embodiment, the CAR binds to B7-H6. In another embodiment, the CAR binds to CA9. In another embodiment, the CAR binds to $\alpha_v\beta_6$ integrin. In another embodiment, the CAR binds to 8H9. In another embodiment, the CAR binds to NCAM. In another embodiment, the CAR binds to fetal acetylcholine receptor.

In another embodiment, the chimeric antigen receptor (CAR) T-cell targets the CD19 antigen, and has a therapeutic effect on subjects with B-cell malignancies, ALL, Follicular lymphoma, CLL, and Lymphoma. In another embodiment, the CAR T-cell targets the CD22 antigen, and has a therapeutic effect on subjects with B-cell malignancies. In another embodiment, the CAR T-cell targets alpha folate receptor or folate receptor alpha, and has a therapeutic effect on subjects with ovarian cancer or epithelial cancer. In another embodiment, the CAR T-cell targets CAIX or G250/CAIX, and has a therapeutic effect on subjects with renal cell carcinoma. In another embodiment, the CAR T-cell targets CD20, and has a therapeutic effect on subjects with Lymphomas, B-cell malignancies, B-cell lymphomas, Mantle cell lymphoma and, indolent B-cell lymphomas. In another embodiment, the CAR T-cell targets CD23, and has a therapeutic effect on subjects with CLL. In another embodiment, the CAR T-cell targets CD24, and has a therapeutic effect on subjects with pancreatic adenocarcinoma. In another embodiment, the CAR T-cell targets CD30, and has a therapeutic effect on subjects with Lymphomas or Hodgkin lymphoma. In another embodiment, the CAR T-cell targets CD33, and has a therapeutic effect on subjects with AML. In another embodiment, the CAR T-cell targets CD38, and has a therapeutic effect on subjects with Non-Hodgkin lymphoma. In another embodiment, the CAR T-cell targets CD44v6, and has a therapeutic effect on subjects with several malignancies. In another embodiment, the CAR T-cell targets CD44v7/8, and has a therapeutic effect on subjects with cervical carcinoma. In another embodiment, the CAR T-cell targets CD123, and has a therapeutic effect on subjects with myeloid malignancies. In another embodiment, the CAR T-cell targets CEA, and has a therapeutic effect on subjects with colorectal cancer. In another embodiment, the CAR T-cell targets EGFRvIII, and has a therapeutic effect on subjects with Glioblastoma. In another embodiment, the CAR T-cell targets EGP-2, and has a therapeutic effect on subjects with multiple malignancies. In another embodiment, the CAR T-cell targets EGP-40, and has a therapeutic effect on subjects with colorectal cancer. In another embodiment, the CAR T-cell targets EphA2, and has a therapeutic effect on subjects with Glioblastoma. In another embodiment, the CAR T-cell targets Erb-B2 or ErbB3/4, and has a therapeutic effect on subjects with Breast cancer and others, prostate cancer, colon cancer, various tumors. In another embodiment, the CAR T-cell targets Erb-B 2,3,4, and has a therapeutic effect on subjects with Breast cancer and others. In another embodiment, the CAR T-cell targets FBP, and has a therapeutic effect on subjects with Ovarian cancer. In another embodiment, the CAR T-cell targets fetal acetylcholine receptor, and has a therapeutic effect on subjects with Rhabdomyosarcoma. In another embodiment, the CAR T-cell targets $G_{D2}$, and has a therapeutic effect on subjects with Neuroblastoma, melanoma, or Ewing's sarcoma. In another embodiment, the CAR T-cell targets GD3, and has a therapeutic effect on subjects with Melanoma. In another embodiment, the CAR T-cell targets HER2, and has a therapeutic effect on subjects with medulloblastoma, pancreatic adenocarcinoma, Glioblastoma, Osteosarcoma, or Ovarian cancer. In another embodiment, the CAR T-cell targets HMW-MAA, and has a therapeutic effect on subjects with Melanoma. In another embodiment, the CAR T-cell targets IL-11Ralpha, and has a therapeutic effect on subjects with Osteosarcoma. In another embodiment, the CAR T-cell targets IL-13Ralpha1, and has a therapeutic effect on subjects with Glioma, Glioblastoma, or medulloblastoma. In another embodiment, the CAR T-cell targets IL-13 receptor alpha2, and has a therapeutic effect on subjects with several malignancies. In another embodiment, the CAR T-cell targets KDR, and has a therapeutic effect on subjects with tumors by targeting tumor neovasculature. In another embodiment, the CAR T-cell targets kappa-light chain, and has a therapeutic effect on subjects with B-cell malignancies (B-NHL, CLL). In another embodiment, the CAR T-cell targets Lewis Y, and has a therapeutic effect on subjects with various carcinomas or epithelial-derived tumors. In another embodiment, the CAR T-cell targets L1-cell adhesion molecule, and has a therapeutic effect on subjects with Neuroblastoma. In another embodiment, the CAR T-cell targets MAGE-A1 or HLA-A1 MAGE A1 and has a therapeutic effect on subjects with Melanoma. In another embodiment, the CAR T-cell targets mesothelin, and has a therapeutic effect on subjects with Mesothelioma. In another embodiment, the CAR T-cell targets CMV infected cells, and has a therapeutic effect on subjects with CMV. In another embodiment, the CAR T-cell targets MUC1, and has a therapeutic effect on subjects with breast or ovarian cancer. In another embodiment, the CAR T-cell targets MUC16, and has a therapeutic effect on subjects with ovarian cancer. In another embodiment, the CAR T-cell targets NKG2D ligands, and has a therapeutic effect on subjects with myeloma, ovarian, and other tumors. In another embodiment, the CAR T-cell targets NY-ESO-1 (157-165) or HLA-A2 NY-ESO-1, and has a therapeutic effect on subjects with multiple myeloma. In another embodiment, the CAR T-cell targets oncofetal antigen (h5T4), and has a therapeutic effect on subjects with various tumors. In another embodiment, the CAR T-cell targets PSCA, and has a therapeutic effect on subjects with prostate carcinoma. In another embodiment, the CAR T-cell targets PSMA, and has a therapeutic effect on subjects with prostate cancer/tumor vasculature. In another embodiment, the CAR T-cell targets ROR1, and has a therapeutic effect on subjects with B-CLL and mantle cell lymphoma. In another embodiment, the CAR T-cell targets TAG-72, and has a therapeutic effect on subjects with adenocarcinomas or gastrointestinal cancers. In another embodiment, the CAR T-cell targets VEGF-$R^2$ or other VEGF receptors, and has a therapeutic effect on subjects with tumors by targeting tumor neovasculature. In another embodiment, the CAR T-cell targets CA9, and has a therapeutic effect on subjects with renal cell carcinoma. In another embodiment, the CAR T-cell targets CD171, and has a therapeutic effect on subjects with renal neuroblastoma. In another embodiment, the CAR T-cell targets NCAM, and has a therapeutic effect on subjects with neuroblastoma. In another embodiment, the CAR T-cell targets fetal acetylcholine receptor, and has a therapeutic effect on subjects with rhabdomyosarcoma. In another embodiment, the CAR binds to one of the target antigens listed in Table 1 of Sadelain et al. (Cancer Discov. 2013 April; 3(4): 388-398), which is incorporated by reference herein in its entirety. In another embodiment, CAR T-cells bind to carbohydrate or glycolipid structures.

In one embodiment the CAR binds to an angiogenic factor, thereby targeting tumor vasculature. In one embodiment, the angiogenic factor is VEGFR2. in another embodiment, the angiogenic factor is endoglin. In another embodiment, an angiogenic factor disclosed herein is Angiogenin; Angiopoietin-1; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF). In another embodiment, an angiogenic factor is an angiogenic protein. In one embodiment, a growth factor is an angiogenic protein. In one embodiment, an angiogenic protein for use in the compositions and methods disclosed herein is Fibroblast growth factors (FGF); VEGF; VEGFR and Neuropilin 1 (NRP-1); Angiopoietin 1 (Ang1) and Tie2; Platelet-derived growth factor (PDGF; BB-homodimer) and PDGFR; Transforming growth factor-beta (TGF-β), endoglin and TGF-β receptors; monocyte chemotactic protein-1 (MCP-1); Integrins αVβ3, αVβ5 and α5β1; VE-cadherin and CD31; ephrin; plasminogen activators; plasminogen activator inhibitor-1; Nitric oxide synthase (NOS) and COX-2; AC133; or Id1/Id3. In one embodiment, an angiogenic protein for use in the compositions and methods disclosed herein is an angiopoietin, which in one embodiment, is Angiopoietin 1, Angiopoietin 3, Angiopoietin 4 or Angiopoietin 6. In one embodiment, endoglin is also known as CD105; EDG; HHT1; ORW; or ORW1. In one embodiment, endoglin is a TGFbeta co-receptor.

In another embodiment, the CAR T-cells bind to an antigen associated with an infectious agent. In one embodiment, the infectious agent is *Mycobacterium tuberculosis*. In one embodiment, said *Mycobacterium tuberculosis* associated antigen is: Antigen 85B, Lipoprotein IpqH, ATP dependent helicase putative, uncharacterized protein Rv0476/MTO4941 precursor or uncharacterized protein R v1334/MT1376 precursor.

In another embodiment, the CAR binds to an antibody. In one embodiment, the CAR T-cell is an "antibody-coupled T-cell receptor" (ACTR). According to this embodiment, the CAR T-cell is a universal CAR T-cell. In another embodiment, the CAR T-cell having an antibody receptor is administered before, after, or at the same time as the antibody is administered and then binds to the antibody, bringing the T-cell in close proximity to the tumor or cancer. In another embodiment, the antibody is directed against a tumor cell antigen. In another embodiment, the antibody is directed against CD20. In another embodiment, the antibody is rituximab.

In another embodiment, the antibody is Trastuzumab (Herceptin; Genentech): humanized IgG1, which is directed against ERBB2. In another embodiment, the antibody is Bevacizumab (Avastin; Genentech/Roche): humanized IgG1, which is directed against VEGF. In another embodiment, the antibody is Cetuximab (Erbitux; Bristol-Myers Squibb): chimeric human-murine IgG1, which is directed against EGFR. In another embodiment, the antibody is Panitumumab (Vectibix; Amgen): human IgG2, which is directed against EGFR. In another embodiment, the antibody is Ipilimumab (Yervoy; Bristol-Myers Squibb): IgG1, which is directed against CTLA4.

In another embodiment, the antibody is Alemtuzumab (Campath; Genzyme): humanized IgG1, which is directed against CD52. In another embodiment, the antibody is Ofatumumab (Arzerra; Genmab): human IgG1, which is directed against CD20. In another embodiment, the antibody is Gemtuzumab ozogamicin (Mylotarg; Wyeth): humanized IgG4, which is directed against CD33. In another embodiment, the antibody is Brentuximab vedotin (Adcetris; Seattle Genetics): chimeric IgG1, which is directed against CD30. In another embodiment, the antibody is 90Y-labelled ibritumomab tiuxetan (Zevalin; IDEC Pharmaceuticals): murine IgG1, which is directed against CD20. In another embodiment, the antibody is 131I-labelled tositumomab (Bexxar; GlaxoSmithKline): murine IgG2, which is directed against CD20.

In another embodiment, the antibody is Ramucirumab, which is directed against vascular endothelial growth factor receptor-2 (VEGFR-2). In another embodiment, the antibody is ramucirumab (Cyramza Injection, Eli Lilly and Company), blinatumomab (BLINCYTO, Amgen Inc.), pembrolizumab (KEYTRUDA, Merck Sharp & Dohme Corp.), obinutuzumab (GAZYVA, Genentech, Inc.; previously known as GA101), pertuzumab injection (PERJETA, Genentech, Inc.), or denosumab (Xgeva, Amgen Inc.). In another embodiment, the antibody is Basiliximab (Simulect; Novartis). In another embodiment, the antibody is Daclizumab (Zenapax; Roche).

In another embodiment, the antibody to which the CAR T-cell is coupled is directed to a tumor or cancer antigen or a portion thereof, that is described herein and/or that is known in the art. In another embodiment, the antibody to which the CAR T-cell is couples is directed to a tumor-associated antigen. In another embodiment, the antibody to which the CAR T-cell is couples is directed to a tumor-associated antigen or a portion thereof that is an angiogenic factor.

In another embodiment, the antibody to which the CAR T-cell is coupled is directed to a tumor or cancer antigen or a portion thereof, that is described herein and/or that is known in the art.

Infections

In another embodiment, a subject as described herein suffers from an infection.

In one embodiment, the present invention provides a method of suppressing, inhibiting, decreasing the risk of, or preventing an infection in a subject comprising contacting one or more cells of said subject with a therapeutically effective amount of a compound that promotes the detachment of HK2 from mitochondria.

In one embodiment, the HK2/mitochondria-detaching compound comprises a jasmonic acid derivative. In another embodiment, the HK2/mitochondria-detaching compound comprises a piperazine derivative. In one embodiment, the compound is represented by the structure of Formula (VII):

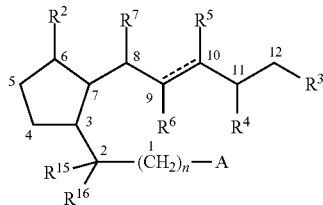

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof. In another embodiment, the compound is represented by the structure of Formula C, as described herein.

In one embodiment, the present invention provides a method of treating an infection in a subject comprising contacting one or more cells of said subject with a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative. In one embodiment, the compound is represented by the structure of Formula (VII):

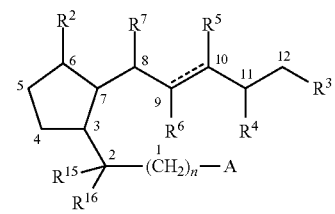

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^1$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof. In another embodiment, the compound is represented by the structure of Formula C, as described herein.

In one embodiment, the present invention provides a method of potentiating the immune response to an infection in a subject with an infection comprising contacting one or more cells of said subject with a therapeutically effective amount of a compound that promotes the detachment of HK2 from mitochondria. In another embodiment, the present invention provides a method of potentiating the immune response to one or more infectious diseases in a subject comprising contacting one or more cells of said subject with a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative. In one embodiment, the compound is represented by the structure of Formula (VII):

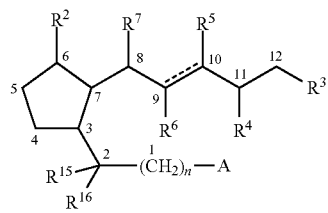

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof. In another embodiment, the compound is represented by the structure of Formula C, as described herein.

In another embodiment, said infection is a microbial infection.

In one embodiment, the microbial infection is a bacterial infection.

In one embodiment, the bacterial infection comprises a *Staphylococcus aureus* infection.

In one embodiment, the bacterial infection comprises a *Mycobacterium tuberculosis* infection.

In another embodiment, the N-acetylglucosamine (NAG) in the peptidoglycan (PGN) of the bacterium is de-acetylated, thereby decreasing the inflammasome activation in response to infection by said bacterium.

In one embodiment, the inflammasome activation is an NLRP3 inflammasome activation.

In another embodiment, said bacterial infection comprises a *Bacillus anthracis* infection.

In one embodiment, the microbial infection is a fungal infection.

In one embodiment, the microbial infection is a *Plasmodium* infection.

In one embodiment, the *Plasmodium* infection is a *Plasmodium falciparum*: infection.

In one embodiment, the *Plasmodium* infection comprises a *Plasmodium falciparum* infection. In another embodiment, the *Plasmodium* infection comprises a *Plasmodium vivax, Plasmodium ovale*, or *Plasmodium malariae* infection. In another embodiment, the *Plasmodium* infection comprises a *Plasmodium knowlesi* infection. In one embodiment, the *Plasmodium* infection causes malaria in said subject.

In another embodiment, said infection is a viral infection.

In one embodiment, the viral infection is a retroviral infection.

In one embodiment, the retroviral infection is a lentivirus infection.

In one embodiment, the lentivirus infection is a Human Immunodeficiency Virus (HIV) infection.

In another embodiment, said subject is afflicted with African Trypanosomiasis ("sleeping sickness"), Cholera, Cryptosporidiosis, Dengue, Hepatitis A, Hepatitis B, Hepatitis C, Acquired Immune Deficiency Syndrome (AIDS), Influenza, Japanese Encephalitis, Leishmaniasis, Malaria, Measles, Meningitis, Onchocerciasis ("river blindness"), Pneumonia, Rotavirus, Schistosomiasis, Shigellosis, Strep Throat, Tuberculosis, Typhoid, Yellow Fever, Ebola Hemorrhagic Fever or West Nile Virus.

In another embodiment, said subject is immunocompromised.

In one embodiment, the subject has an immunodeficiency disorder.

In one embodiment, the immunodeficiency disorder is congenital (primary).

In one embodiment, the congenital immunodeficiency disorder comprises X-linked agammaglobulinemia (XLA), common variable immunodeficiency (CVID), or severe combined immunodeficiency (SCID).

In one embodiment, the immunodeficiency disorder is acquired (secondary).

In one embodiment, the acquired immunodeficiency disorder comprises immunodeficiency resulting from a severe burn, chemotherapy, radiation, diabetes, malnutrition, AIDS, or an immune-complex disease.

In one embodiment, the immune-complex disease comprises viral hepatitis.

In one embodiment, the acquired immunodeficiency disorder comprises a cancer of the immune system.

In one embodiment, the cancer of the immune system comprises leukemia or multiple myeloma.

In one embodiment, the subject has a disease or condition linked to a primary immunodeficiency disorder.

In one embodiment, the disease or condition comprises ataxia-telangiectasia, Chediak-Higashi syndrome, combined immunodeficiency disease, complement deficiencies, DiGeorge syndrome, hypogammaglobulinemia, Job syndrome, leukocyte adhesion defects, panhypogammaglobulinemia, Bruton's disease, congenital agammaglobulinemia, selective deficiency of IgA, Wiskott-Aldrich syndrome, HIV, or cancer therapy.

In one embodiment, the subject has a brain injury.

In another embodiment, contacting one or more cells of said subject comprises the step of administering a composition comprising said compound to said subject.

Pharmaceutical Compositions

Although the hexokinase 2 (HK2)/mitochondria-detaching compounds can be administered alone, it is contemplated, in one embodiment, that these compounds will be administered in a pharmaceutical composition containing the hexokinase 2 (HK2)/mitochondria-detaching compound together with a pharmaceutically acceptable carrier or excipient.

In one embodiment, the active ingredient is a jasmonic derivative in the pharmaceutical composition is dissolved in any acceptable lipid carrier (e.g., fatty acids, oils to form, for example, a micelle or a liposome). In one embodiment, the composition additionally comprises at least one other chemotherapeutic agent.

In one embodiment, at least one of the excipients is a non-aqueous excipient.

In one embodiment, a compound as described herein which in one embodiment is represented by the structure of Formula (VII), may be mixed with stabilizing excipients useful for topical administration in a formulation which is essentially free of compounds bearing a nucleophilic character like water, alcoholic solvents and carboxylic acids. In some embodiments, the topical pharmaceutical composition of the present invention comprises a therapeutically effective amount of a compound as described herein, which in one embodiment is represented by the structure of Formula (VII), or a pharmaceutically acceptable salt or solvate thereof, and at least one pharmaceutically acceptable excipient selected from the group consisting of a glycol diester with a saturated or unsaturated fatty acid, a triglyceride, an aprotic organic solvent, and any combination thereof, and optionally an oil and/or a wax.

In one embodiment, the pharmaceutically acceptable excipient comprises a compound represented by the structure of Formula (VIII):

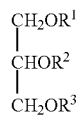

wherein:
R$^1$, R$^2$ and R$^3$ are each selected from the group consisting of H and R$^4$—COO—, wherein at least two of R$^1$, R$^2$ and R$^3$ are R$^4$—COO; and
R$^4$—COO— is the residue of a saturated or unsaturated fatty acid.

In another embodiment, the pharmaceutically acceptable excipient comprises a triglyceride of Formula (VIII) or a combination thereof wherein R$^1$, R$^2$ and R$^3$ are each R$^4$—C(═O)—; and R$^4$—C(═O)O— is the residue of an unsaturated or saturated fatty acid.

In some embodiments, the pharmaceutically acceptable excipient comprises a triglyceride with a medium chain (e.g., C$_8$-C$_{12}$) saturated or unsaturated fatty acid. In one embodiment, the pharmaceutically acceptable excipient is caprylic/capric triglyceride (in one embodiment Labrafac lipophile WL 1349).

In another embodiment, the pharmaceutically acceptable excipient comprises a propylene glycol diester with a saturated or unsaturated fatty acid. In one embodiment, the fatty acid is a medium chain (e.g., C$_8$-C$_{12}$) saturated or unsaturated fatty acid. In one embodiment, the pharmaceutically acceptable excipient is propylene glycol dicaprylate (in one embodiment, Labrafac PG).

In one embodiment, the organic solvent is dimethylsulfoxide (DMSO).

Compositions of the present invention may further comprise optional components such as lipid carriers such as oils or waxes so as to provide a semi-solid consistency as desired. Additional inactive excipients such as preservatives, anti-oxidants, perfumes and the like may also be added.

Oils that can be used as optional components in the compositions of the present invention include, but are not limited to, petrolatum (petroleum jelly), vegetable oil, fruit oil, plant oil, animal oil, mineral oil, coconut oil, olive oil, lanolin, peanut oil, hydrogenated and sulphated oils such as cottonseed oil, soybean oils, almond oil, sesame oil, and the like. In another embodiment, the oil comprises corn oil, peanut oil, coconut oil, grape seed oil, sunflower oil, lemon oil, orange oil, peppermint oil, palm kernel oil, castor oil, hydrogenated cottonseed oil, hydrogenated soy oil, hydrogenated soybean oil, hydrogenated vegetable oil, partially hydrogenated soybean oil, partially hydrogenated palm oil, hydrogenated castor oil, light mineral oil, mineral oil, or a combination thereof.

Waxes that can be used as optional components in the compositions of the present invention include, but are not limited to, paraffin wax, beeswax, carnauba wax, cetyl ester wax, microcrystalline wax, spermaceti wax, and the like.

In some embodiments, the composition of the invention comprises the compound as described herein, propylene glycol dicaprylate (Labrafac PG), caprylic/capric triglyceride (Labrafac lipophile WL 1349), dimethylsulfoxide (DMSO), petrolatum and paraffin wax.

In some embodiments, the composition of the invention comprises a compound as described herein in an amount of from about 5% w/w to about 30% w/w. In some embodiments, the composition of the invention comprises a compound as described herein in an amount of about 5% w/w. In some embodiments, the composition of the invention comprises a compound as described herein in an amount of about 10% w/w. In some embodiments, the composition of the invention comprises a compound as described herein in an amount of about 15% w/w. In some embodiments, the composition of the invention comprises a compound as described herein in an amount of about 20% w/w. In one embodiment, the compound is represented by the structure of Formula (VII).

In some embodiments, the composition of the invention comprises a compound as described herein in an amount of from about 5% to about 30% w/w; propylene glycol dicaprylate in an amount of from about 1% to about 10% w/w; caprylic/capric triglyceride in an amount of from about 30% to about 50% w/w; dimethyl sulfoxide in an amount of from about 0% to about 10% w/w; petrolatum in an amount of from about 20% to about 50% w/w; and paraffin wax in an amount of from about 0 to about 10% w/w.

In some embodiments, the composition of the invention comprises a compound as described herein in an amount of about 5% w/w; propylene glycol dicaprylate in an amount of about 10% w/w; caprylic/capric triglyceride in an amount of about 50% w/w; dimethyl sulfoxide in an amount of about 1% w/w; petrolatum in an amount of about 30% w/w; and paraffin wax in an amount of about 4% w/w.

In other embodiments, the composition of the invention comprises a compound as described herein in an amount of about 10% w/w; propylene glycol dicaprylate in an amount of about 7.5% w/w; caprylic/capric triglyceride in an amount of about 47.5% w/w; dimethyl sulfoxide in an amount of about 1% w/w; petrolatum in an amount of about 30% w/w; and paraffin wax in an amount of about 4% w/w.

In other embodiments, the composition of the invention comprises: a compound as described herein in an amount of about 15% w/w; propylene glycol dicaprylate in an amount of about 5% w/w; caprylic/capric triglyceride in an amount of about 45% w/w; dimethyl sulfoxide in an amount of about 1% w/w; petrolatum in an amount of about 30% w/w; and paraffin wax in an amount of about 4% w/w.

In certain embodiments, the composition of the invention comprises a compound as described herein in an amount of about 20% w/w; propylene glycol dicaprylate in an amount of about 2.5% w/w; caprylic/capric triglyceride in an amount of about 42.5% w/w; dimethyl sulfoxide in an amount of about 1% w/w; petrolatum in an amount of about 30% w/w; and paraffin wax in an amount of about 4% w/w.

In some embodiments, the composition described above is essentially free of water, alcoholic solvents and carboxylic acids.

The pharmaceutically acceptable excipients according to the principles of the present invention may be a triglyceride, a glycol diester or a combination thereof. In some embodiments, the triglyceride and/or the glycol diester comprise saturated or unsaturated fatty acids. The term "saturated fatty acid" encompasses a carboxylic acid with an elongated aliphatic saturated chain. The term "unsaturated fatty acid" encompasses a carboxylic acid with an elongated aliphatic chain which have one or more double bonds between the carbon atoms. The length of the carbon chain may vary, but may generally be between 4 and 30 carbon atoms ($C_4$-$C_{30}$). In some embodiments, the triglyceride and/or glycol diester comprises medium chain (e.g., $C_8$-$C_{12}$) saturated or unsaturated fatty acids.

The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, or via a suppository. Such compositions are prepared in a manner well known in the pharmaceutical art and comprise as an active ingredient at least one compound of the present invention as described hereinabove, and a pharmaceutically acceptable excipient or a carrier.

In one embodiment, the term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention, the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound for use in the present invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. In one embodiment, water is a preferred carrier when the pharmaceutical composition is administered intravenously. Saline solutions and aqueous dextrose and glycerol solutions can also be employed as liquid carriers, particularly for injectable solutions.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration. In one embodiment, the topical composition comprises an ointment. In another embodiment, the topical composition comprises a cream. In another embodiment, the topical composition comprises a lotion. In another embodiment, the topical composition comprises a gel. In another embodiment, the topical composition comprises a paste. In another embodiment, the topical composition comprises a drop. In another embodiment, the topical composition comprises a foam. For topical administration to body surfaces using, for example, creams, gels, drops, ointments and the like, the compounds of the present invention can be prepared and applied in a physiologically acceptable diluent with or without a pharmaceutical carrier.

In one embodiment, the present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

In one embodiment, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. In one embodiment, administration is localized. In another embodiment, administration is systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In one embodiment, a compound of the invention is administered in combination with a biodegradable, biocompatible polymeric implant, which releases the compound over a controlled period of time at a selected site. Examples of polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Alternatively, the jasmonate derivatives of the present invention can be used in hemodialysis such as leukophoresis and other related methods, e.g., blood is drawn from the patient by a variety of methods such dialysis through a column/hollow fiber membrane, cartridge etc, is treated with the jasmonate derivatives Ex-vivo, and returned to the patient following treatment. Such treatment methods are well known and described in the art. See, e.g., Kolho et al. (J. Med. Virol. 1993, 40(4): 318-21); Ting et al. (Transplantation, 1978, 25(1): 31-3); the contents of which are hereby incorporated by reference in their entirety.

As used herein, the term "administering" refers to bringing in contact with a compound of the present invention. In one embodiment, the compositions are applied locally. In another embodiment, the compositions are applied systemically. Administration can be accomplished to cells or tissue cultures, or to living organisms, for example humans.

A "therapeutic" treatment is a treatment administered to a subject who exhibits signs of pathology for the purpose of diminishing or eliminating those signs.

In one embodiment, compounds and compositions of the present inventions are provided to a subject in a therapeutically effective amount. In one embodiment, a "therapeutically effective amount" of a compound of the invention is that amount of compound which is sufficient to provide a beneficial effect to the subject to which the compound is administered.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

According to any of the methods of the present invention and in one embodiment, the subject is human. In another embodiment, the subject is mammalian. In another embodiment, the subject is a primate, which in one embodiment, is a non-human primate. In another embodiment, the subject is murine, which in one embodiment is a mouse, and, in another embodiment is a rat. In another embodiment, the subject is canine, feline, bovine, equine, caprine, ovine, porcine, simian, ursine, vulpine, or lupine. In one embodiment, the subject is a chicken or fish.

Doses and Routes of Administration

In one embodiment, the composition is formulated for parenteral administration.

In another embodiment, the composition is formulated for intravenous, subcutaneous, or intramuscular administration. In another embodiment, the composition is formulation for per os (P.O.) or oral administration. In one embodiment, is formulated for topical administration.

In one embodiment, the jasmonic derivatives as described herein are formulated for subcutaneous injection.

In one embodiment, the piperazine derivatives, as described herein are formulated for oral administration.

In one embodiment, the composition comprises 5% of the compound as described herein. In another embodiment, the composition comprises 10% of the compound as described herein. In another embodiment, the composition comprises 15% of the compound as described herein. In another embodiment, the composition comprises 20% of the compound as described herein. In another embodiment, the composition comprises 30% of the compound as described herein. In another embodiment, the composition comprises 40% of the compound as described herein. In another embodiment, the composition comprises 50% of the compound as described herein. In one embodiment, the compound is the compound represented by the structure of Formula (VII).

In a further embodiment, the compound as described herein is formulated as 250 mg of a 5%, 10%, 20%, 30%, 40% or 50% cream, gel, ointment or paste. In one embodiment, the compound is the compound represented by the structure of Formula (VII).

In another embodiment, the compound as described herein is formulated as 200 mg of a 5%, 10%, 20%, 30%, 40% or 50% cream, gel, ointment or paste. In one embodiment, the compound is the compound represented by the structure of Formula (VII).

In one embodiment, the compound as described herein is administered once per day. In another embodiment, the compound as described herein is administered twice per day. In another embodiment, the compound as described herein is administered three times per day. In another embodiment, the compound as described herein is administered four times per day. In another embodiment, the compound as described herein is administered once every two days, once every three days, twice a week, once a week, once every 2 weeks, once every 3 weeks. In one embodiment, the compound is the compound represented by the structure of Formula (VII). In another embodiment the compound is the compound represented by the structure of Formula (II), which in one embodiment comprises the compounds of Formula (20-24).

In one embodiment, the compound as described herein is administered for 7 days to 28 days. In another embodiment, the compound as described herein is administered for 7 days to 8 weeks. In another embodiment, the compound as described herein is administered for 7 days to 50 days. In another embodiment, the compound as described herein is administered for 7 days to six months. In another embodiment, the compound as described herein is administered for 7 days to one and half years. In another embodiment, the compound as described herein is administered for 14 days to 12 months. In another embodiment, the compound as described herein is administered for 14 days to 3 years. In another embodiment, the compound as described herein is administered for several years. In another embodiment, the compound as described herein is administered for one month to six months. In one embodiment, the compound is the compound represented by the structure of Formula (VII). In another embodiment the compound is the compound represented by the structure of Formula (II), which in one embodiment comprises the compounds of Formula (20-24).

In one embodiment, the compound as described herein is administered for 7 days. In another embodiment, the compound as described herein is administered for 14 days. In another embodiment, the compound as described herein is administered for 21 days. In another embodiment, the compound as described herein is administered for 28 days. In another embodiment, the compound as described herein is administered for 50 days. In another embodiment, the compound as described herein is administered for 56 days. In another embodiment, the compound as described herein is administered for 84 days. In another embodiment, the compound as described herein is administered for 90 days. In another embodiment, the compound as described herein is administered for 120 days. In one embodiment, the compound is the compound represented by the structure of Formula (VII). In another embodiment the compound is the compound represented by the structure of Formula (II), which in one embodiment comprises the compounds of Formula (20-24).

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. In one embodiment, the dosage will be within the range of 0.01-1000 mg/kg of body weight, in another embodiment, 0.1 mg/kg to 100 mg/kg, in another embodiment, 1 mg/kg to 10 mg/kg, and, in another embodiment, 100-400 mg/kg. Effective doses may be extrapolated from dose-response curves derived from in vitro or animal model test bioassays or systems.

As described hereinabove, in one embodiment, methods of the present invention further comprise the step of contacting one or more cells of said subject with a therapeutic agent. In one embodiment, the chemotherapeutic agent is administered prior to administration the compound as described herein. In another embodiment, the chemotherapeutic agent is administered concurrently with the compound represented by the structure as described herein. In another embodiment, the chemotherapeutic agent is administered after administration the compound as described herein. In one embodiment, the compound is the compound represented by the structure of Formula (VII). In another embodiment the compound is the compound represented by the structure of Formula (II), which in one embodiment comprises the compounds of Formula (20-24).

In another embodiment, the present invention provides a method of inducing cell pyroptosis in a subject comprising contacting one or more cells of said subject with a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

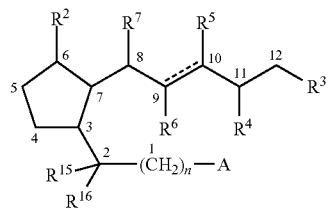

wherein A is COR$^1$; R$^1$ is an unsubstituted or substituted heteroaryloxy; R$^2$ is selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$, oxo and NR$^{9a}$R$^{9b}$; R$^3$, R$^4$, R$^5$, R$^6$ and R$^7$ are each independently selected from the group consisting of hydrogen, halogen, unsubstituted or substituted C$_1$-C$_{12}$ alkyl, unsubstituted or substituted C$_1$-C$_{12}$ haloalkyl, unsubstituted or substituted C$_3$-C$_8$ cycloalkyl, unsubstituted or substituted aryl, unsubstituted or substituted heteroaryl, OR$^8$ and NR$^{9a}$R$^{9b}$, or R$^5$ and R$^6$ together with the carbons to which they are attached form a C$_3$-C$_8$ cycloalkyl or a C$_3$-C$_8$ cycloalkyl substituted by halo; or one of R$^5$ and R$^6$ represents an oxygen atom which is bonded to C$_6$, thereby forming an oxygen-containing 6 or 5 membered heterocyclic ring, respectively; wherein the bond between C$_9$ and C$_{10}$ can be a single or double bond; R$^8$, R$^{9a}$ and R$^{9b}$ are each independently selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, glucosyl, or R$^{9a}$ and R$^{9b}$ can together with the nitrogen to which they are attached form an unsubstituted or substituted heterocyclic or heteroaromatic ring optionally containing one or more additional heteroatom selected from O, N and S; R$^{15}$ and R$^{16}$ are each hydrogen; and n is selected from 0, 1 and 2; including salts, hydrates, solvates, polymorphs, optical isomers, geometrical isomers, enantiomers, diastereomers, and mixtures thereof. In another embodiment, the compound is represented by the structure of Formula C, as described herein.

In one embodiment, pyroptosis is a form of cell death that is distinct from apoptosis.

In one embodiment, administration of an HK2/mitochondria-detaching compound as described herein leads to dissociation of HK2 from VDAC. In another embodiment, administration of an HK2/mitochondria-detaching compound leads to activation of an inflammasome, which, in one embodiment, leads to an immune response directed to cancer cells. In another embodiment, administration of the compound of an HK2/mitochondria-detaching compound leads to apoptosis, which in one embodiment, leads to the death of cancer cells. In another embodiment, administration of an HK2/mitochondria-detaching compound leads to reduced glycolysis. In one embodiment, the HK2/mitochondria-detaching compound comprises a jasmonic acid derivative. In one embodiment, the jasmonic acid derivative comprises a compound represented by the structure of Formula (VII) as described herein. In another embodiment, the jasmonic acid derivative comprises a compound represented by the structure of Formula C, as described herein. In another embodiment, the HK2/mitochondria-detaching compound comprises a piperazine derivative.

In one embodiment, stereoisomers of the jasmonate ester derivatives are contemplated either in admixture or in pure or substantially pure form. The jasmonate derivatives can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R, S, D or d or L or l or d,l or D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.*, 66: 1-19, 1977. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is also contemplated.

The present invention also includes solvates of the compounds of the present invention and salts thereof "Solvate" means a physical association of a compound of the invention with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR or Raman spectra, melting point, and the like.

Kits

In another embodiment, the present invention provides a kit for activating an immune response comprising a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

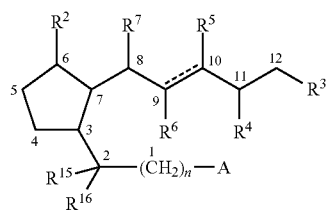

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use for activating an inflammatory response, as described herein. In another embodiment, the compound is represented by the structure of Formula C, as described herein.

In another embodiment, the present invention provides a kit for activating a cell-mediated immune response comprising a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

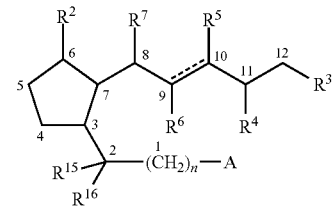

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a}$ $R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use for activating an inflammatory response, as described herein. In another embodiment, the compound is represented by the structure of Formula C, as described herein.

In another embodiment, the present invention provides a kit for activating an inflammatory response comprising a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

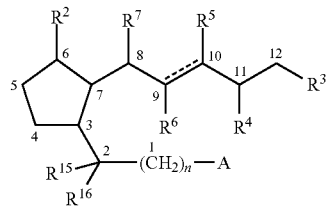

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use for activating an inflammatory response, as described herein. In another embodiment, the compound is represented by the structure of Formula C, as described herein.

In another embodiment, the present invention provides a kit for activating an inflammasome-mediated immune response comprising a therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

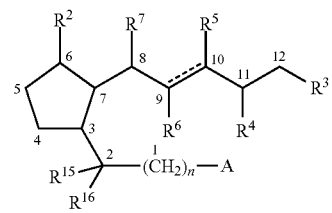

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use for activating an inflammasome-mediated immune response, as described herein. In another embodiment, the compound is represented by the structure of Formula C, as described herein.

In another embodiment, the present invention provides a kit for treating a cancer comprising therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

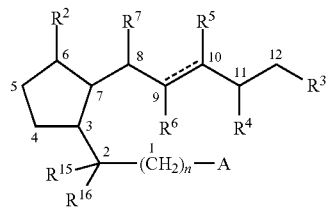

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use for treating said cancer, as described herein. In another embodiment, the kit comprises additional containers comprising additional cancer therapies as described herein. In another embodiment, the compound is represented by the structure of Formula C, as described herein.

In another embodiment, the present invention provides a kit for treating an infection comprising therapeutically effective amount of a compound that promotes the detachment of HK2 from mitochondria. In one embodiment, the HK2/mitochondria-detaching compound comprises a jasmonic acid derivative. In another embodiment, the HK2/mitochondria-detaching compound comprises a piperazine derivative, which in one embodiment, is represented by the structure of Formula (II). In one embodiment, the compound is represented by the structure of Formula (VII):

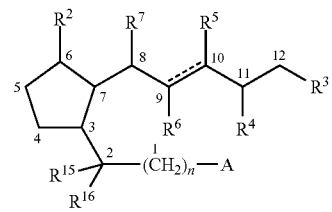

wherein A is $COR^1$; $R^1$ is an unsubstituted or substituted heteroaryloxy; $R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a} R^{9b}$; $R^3$, $R^4$, $R^5$, $R^6$ and $R^7$ are each independently selected from the group consisting of hydrogen, halogen, unsubstituted or substituted $C_1$-$C_{12}$ alkyl, unsubstituted or substituted $C_1$-$C_{12}$ haloalkyl, unsubstituted or substituted $C_3$-$C_8$ cycloalkyl, unsubstituted or substituted aryl, unsubstituted or substituted heteroaryl, $OR^8$ and $NR^{9a} R^{9b}$, or $R^5$ and $R^6$ together with the carbons to which they are attached form a $C_3$-$C_8$ cycloalkyl or a $C_3$-$C_8$ cycloalkyl substituted by halo; or one of $R^5$ and $R^6$ represents an oxygen atom which is bonded to $C_6$, thereby forming an oxygen-containing 6 or 5 membered heterocyclic ring, respectively; wherein the bond between $C_9$ and $C_{10}$ can be a single or double bond; $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; $R^{15}$ and $R^{16}$ are each hydrogen; and n is selected from 0, 1 and 2; including salts, hydrates, solvates, polymorphs, optical isomers, geometrical isomers, enantiomers, diastereomers, and mixtures thereof, and instructions for use to treat an infection as described herein. In another embodiment, the compound is represented by the structure of Formula C, as described herein.

In one embodiment, the kit as described herein comprises a jasmonic derivative formulated for subcutaneous administration. In one embodiment, the kit comprises two vials, wherein the first vial contains the jasmonic derivative and the second vial contains a solvent suitable for subcutaneous injections, which in one embodiment comprises a hydrophobic solvent and, in another embodiment, comprises a mixed hydrophobic/polar solvent. In one embodiment, the content of the vials will be mixed by the nurse shortly before administration.

In one embodiment, the kit comprises additional containers comprising additional cancer therapeutics as described herein.

Any patent, patent application publication, or scientific publication, cited herein, is incorporated by reference herein in its entirety.

The following examples are presented in order to more fully illustrate the uses described herein.

EXAMPLES

Example 1

Topical Formula C Treatment in the Mouse B16-F10 Melanoma Model Inhibits Tumor Growth and Increases Inflammation Cell Lines Mouse melanoma (B16-F10) cells were used. Mouse B16-F10 melanoma cells were maintained in DMEM. Media was supplemented with 10% heat-inactivated FCS, penicillin (100 U/ml), streptomycin (100 µg/ml), Sodium pyruvate (2 mM), and L-glutamine (4 mM). Confluent cultures were washed with PBS, detached with trypsin (0.25%), centrifuged, and subcultured in 96-well microtiter test plates.

Animal Studies

Female C57Bl/6 mice at 8 weeks of age were purchased from Harlan, Jerusalem, Israel. The animals were housed (6 or 7/cage) under controlled conditions (temperature, light, humidity) and given food and water ad libitum. After 14 days of acclimatization, the animals were inoculated with $0.25*10^6$ B16-F10 melanoma cells/mouse in 30 µl PBS under the skin of the right ear of each mouse.

The mice were inoculated with B16-F10 melanoma cells and divided randomly into three groups (9 mice each): a) B16-F10 inoculated, untreated; and b) B16-F10 inoculated, Formula C (50% v/v in olive oil) treated The treatment was initiated when the tumors reached the target volume of approximately 1 mm$^3$. Drug was topically administered to the area of the tumor daily for 18 days.

Inflammation Score

Inflammation was graded on a scale of 0-4 as: 0 (absence of inflammation), 1 (redness), 2 (tissue inflammation), 3 (pronounced tissue inflammation), and 4 (damage to the ear).

Results

Figure 1:
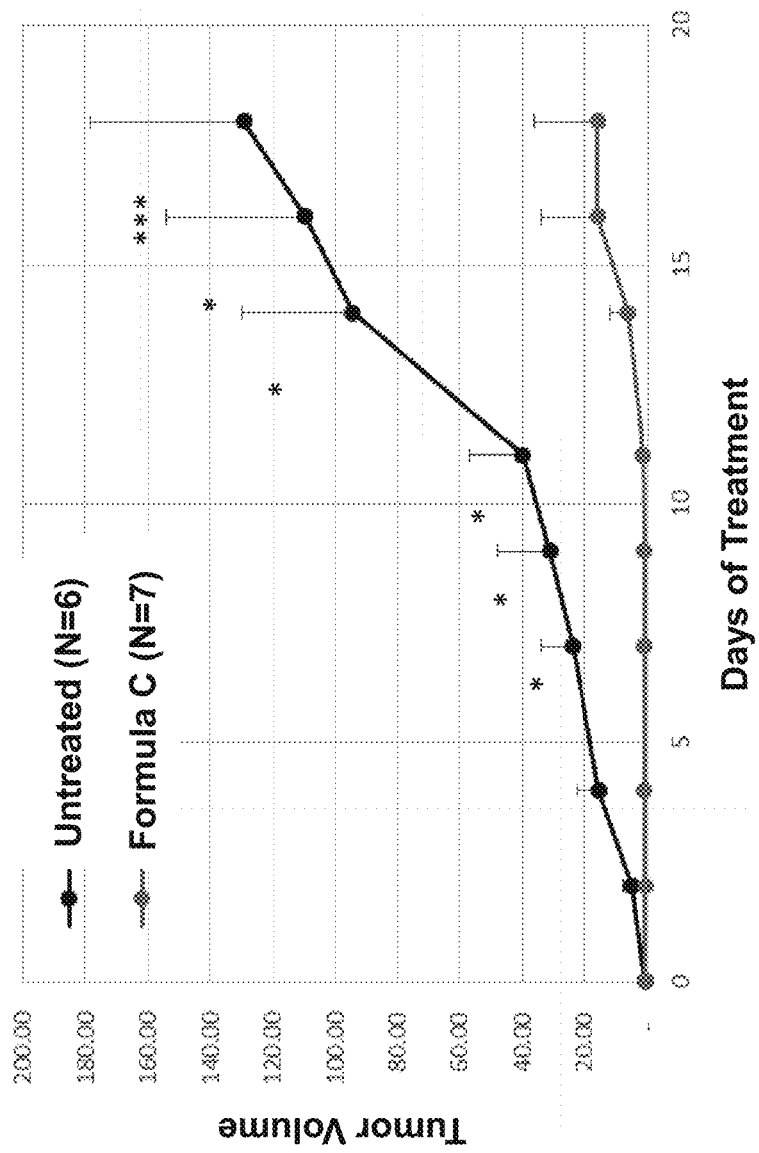
FIG. 1. Efficacy of topical Formula C treatment on tumor volume in the mouse B16-F10 melanoma model. * p≤0.05, *** p≤0.001.

Untreated, B16-F10-inoculated mice demonstrated a steadily increasing tumor volume over the first 18 days of treatment (FIG. 1). In contrast, mice treated with 50% Formula C showed no tumor growth for 11 days, and thereafter only slight increase in tumor volume, which was significantly lower than the tumor volume in the untreated group (FIG. 1).

There is evidence to suggest the inflammatory system may inhibit the development of cancer, possibly via cancer-associated recognition events. The host may have a dedicated mechanism to perceive and eliminate transformed cells. In addition, adaptive immune recognition of tumor-associated and specific antigens also may be an important means by which the immune and inflammatory systems control the development of cancer.

Therefore, the effect of Formula C treatment on ear inflammation in B16-F10 melanoma mice was examined. Untreated B16-F10 melanoma mice did not exhibit any significant inflammation, as determined by inflammation score (inflammation score of 0; FIG. 2). In contrast, B16-F10 melanoma mice treated topically with Formula C exhibited increased inflammation over the course of treatment, attaining an average inflammation score of about 3 by about the 15$^{th}$ day of treatment and increasing to over 3 before the 18$^{th}$ day of treatment (FIG. 2).

Formula C is therefore effective in limiting tumor growth and increases inflammation, which may promote an effective immune response against tumor cells.

Example 2

Topical Formula C Treatment in the AK/cSCC Mouse Model Triggers Immune Response

Topical Formulations

The formulation ingredients for vehicle, 2.5%, and 5% Formula C ointment consisted of: 32% Gelucire44/14® (Gattefossé, Saint-Priest, France), and 68% combined Labrasol® (Gattefossé, Saint-Priest, France) with corresponding amount of Formula C (w/w). New ointments were prepared every 2 weeks. The 40% topical solution was prepared just prior to use by mixing (w/w) 60% propylene glycol (Sigma, St. Louis, MO, USA) with 40% Formula C.

Animal Studies

Female SKH-1 mice were obtained from Charles River Laboratories (Wilmington, NC). Mice were treated and managed at Pharmaseed Ltd. (Ness Ziona, Israel).

Experimental Procedure

UVB-induced skin damage was adopted from previous publications. Forty-eight SKH-1 hairless female mice were chronically exposed to 1.25 times the Minimal Erythemal Dose (MED) of UVB radiation. Lamp VL-6.M was used, irradiating at 312 nm with an intensity of 0.89 mW/cm2 (validated on Day 44) at a distance of 15 cm. Determination of UVB irradiation Minimal Erythemal Dose (MED) was performed prior to the beginning of the study. Animals were UVB irradiated for different duration (starting at 30 sec) and the presence of erythema was recorded 24 and 48 hours later. 1.25 times the MED of UVB irradiation was established to be equal to an exposure time of 5 min. Mice were UVB irradiated for 4-5 min at each irradiation session during the 16 weeks of pre-treatment disease induction. Prior to every irradiation session, the lamp was turned on for 5 min to ensure it reaches its maximal intensity. The irradiation schedule was five times a week for two weeks, one week off, and then three times a week through week 16. By that time, more than 60% of the animals had developed at least one SCC lesion. Three days after the final irradiation dose, the mice were randomly assigned to 1 of 4 treatment groups (N=12 mice/group), with similar tumor burden distribution between groups, and a 50-day treatment phase started. The 6 cm$^2$ (2×3 cm) treatment area was marked on the back of the mice with a black eight points rectangle tattoo. Five spare mice with the highest tumor burden were excluded from the main study. Treatment groups included: vehicle, 2.5% or 5% Formula C ointment, 50 µl of which was applied once-daily for 50 days, or 50 µl of 40% Formula C topical solution applied once-daily for the first 5 days of every three-week cycle (total of three treatment cycles). Following administration, each animal was placed in individual cage without bedding for 1.5 hours, until the ointment was absorbed.

IHC, Histology and Semi-Quantitative Analysis of IHC Slides

Histopathological analysis and IHC was performed according to standard protocols. Primary antibodies used: Rabbit anti-CD3 (SP7), rabbit anti-F4/80 (SB-M3072, SB-M4152, Nordic Biosite, Täby, Sweden), mouse anti-Langerin/CD207 (DDX0361, Dendritics, Lyon, France). A polymer system was used as a secondary antibody (KDB-10046 and KDB-10007, Nordic Biosite, Täby, Sweden). Semi-quantitative analysis was done in a blinded manner by a single experienced pathologist scoring ×40 high power fields, 7 different fields per slide.

Statistical Analysis

Statistical analysis was carried out using Graphpad Prism version 5.03 (Graphpad Software, San Diego, CA).

Results

Histopathology H&E staining established the presence of mild inflammation in all skin samples that were exposed to prolonged UVB radiation (compared to skin of naïve control mice), without apparent difference in overall inflammation between vehicle-treated and Formula C-treated groups. However, a detailed analysis of the distribution of various immune cells in the treated skin revealed statistically significant changes. A statistically significant, dose-related increase in mast cells was observed in the skin of Formula C-treated mice compared to vehicle-treated mice (FIG. 3A). A statistically-significant increase was also observed for CD3+ T cells (FIG. 3B) and for Langerin+ dendritic cells (FIG. 3C) between the vehicle-treated group and the Formula C high dose (40%) group, trending also at lower doses. There was no change in F4/80 general staining for macrophages (data not shown).

Example 3

Formula C Treatment Induced IL-1β Secretion from Activated Macrophages

The human monocyte cell line, THP-1, was grown in 10% FCS in RPMI medium. Cells were plated in 24 well plate, $5*10^6$ cells/well and were differentiated to macrophages in the presence of 0.5 uM PMA (phorbol 12-myristate 13-acetate) for 24 hr. Media was replaced to contain LPS (10 ug/mL), 24 hr stimulation. ATP was added for 2 hours. Supernatants were collected and assayed by ELISA for the presence of IL-1β.

Figure 4:
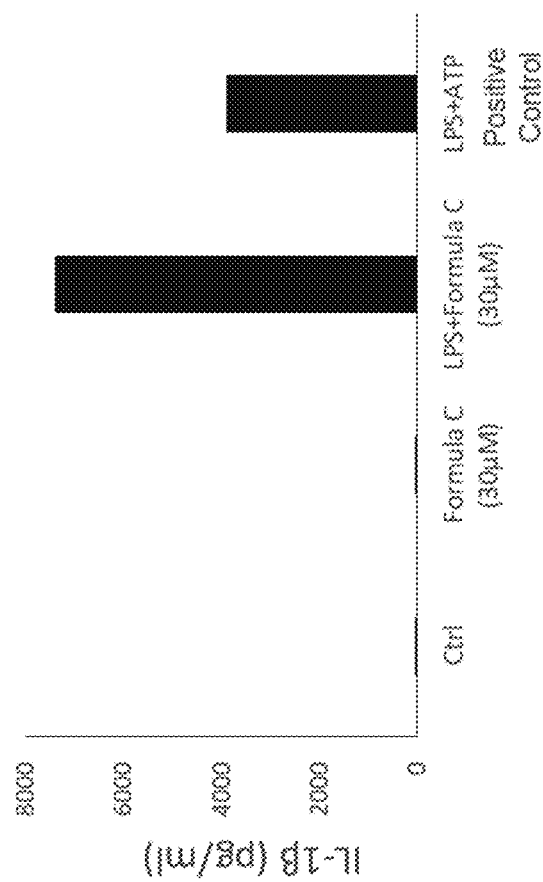
FIG. 4. Formula C stimulates IL-1β secretion in activated human macrophages in vitro. THP-1 human monocytes were differentiated to mature macrophages and stimulated with LPS (Lipopolysaccharide) followed by Formula C treatment. Secreted IL-1β was analyzed in the culture medium by ELISA.
Figure 5B:
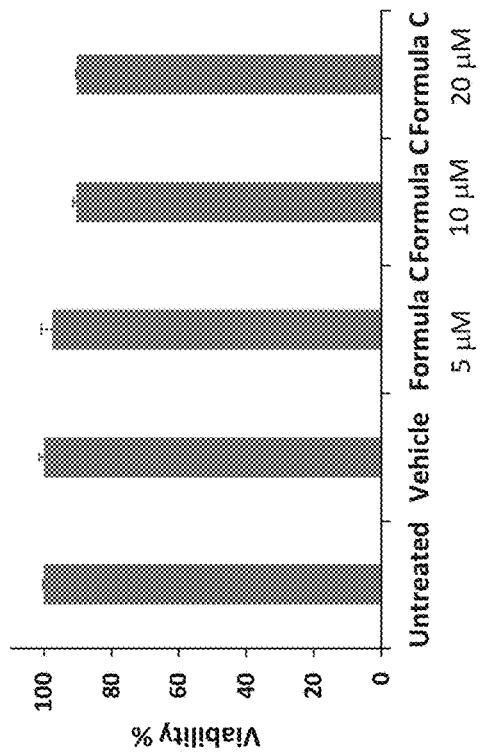
FIG. 5B. The effect of Formula C treatment on the viability of primary bone marrow-derived macrophages from Balb/C mouse.
Figure 5D:
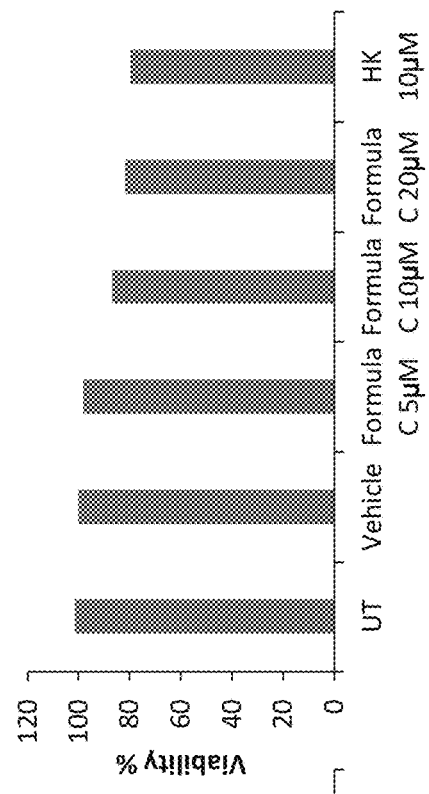
FIG. 5D. The effect of Formula C treatment on the viability of primary bone marrow-derived macrophages from C57BL mouse. UT, untreated. HK (hexokinase peptide) serves as a positive control.

Formula C treatment induced IL-1β secretion from human activated macrophages (FIG. 4). This strongly supports the hypothesis that Formula C activates the NLRP3 inflammasome which results in IL-1β secretion and stimulation of the immune system.

BALB/C mouse bone marrow-derived macrophages (BMDM) or C57BL mouse bone marrow-derived macrophages were seeded at $3\times10^4$ cells/well in 96 well plates. The following day, cells were stimulated with interferon-gamma (IFNγ) overnight 50 ng/ml. Then Ultra-pure LPS (100 ng/ml) was added for 4 hours, followed by compound treatment for overnight, except for ATP (all compounds were added on top); ATP for 40 min. ELISA was performed on supernatants for mouse IL-1β detection. ATP and 2-DG were used as positive controls. No signal without IFN-γ even when seeded at 100,000 cells per well.

Figure 5A:
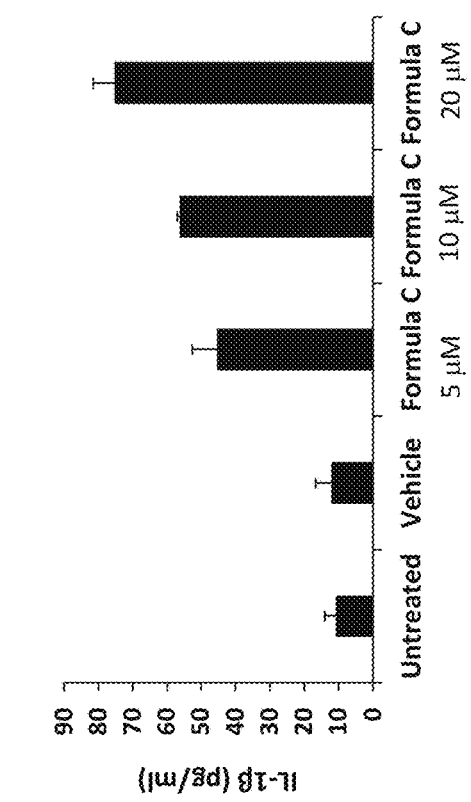
FIG. 5A. Formula C dose-dependently stimulates IL-1β secretion in primary bone marrow-derived macrophages from Balb/C mouse. Secreted IL-1β was analyzed in the culture medium by ELISA.
Figure 5C:
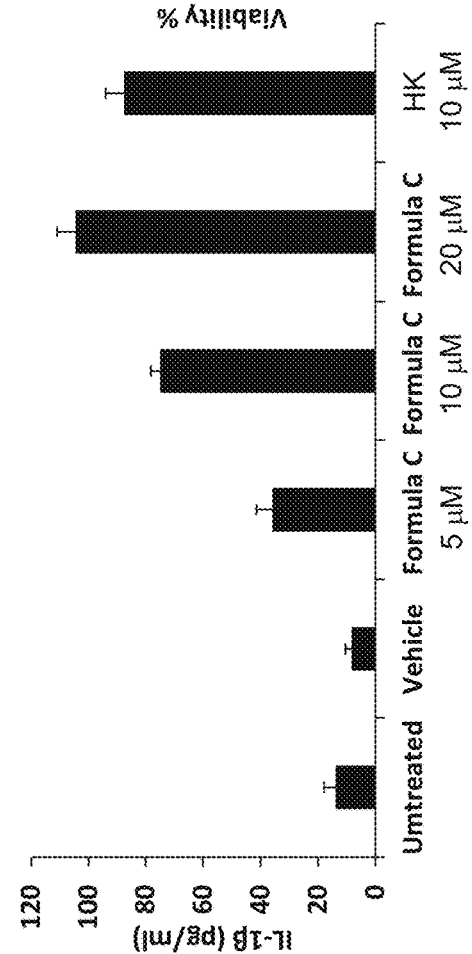
FIG. 5C. Formula C dose-dependently stimulates IL-1β secretion in primary bone marrow-derived macrophages from C57BL mouse. Secreted IL-1β was analyzed in the culture medium by ELISA. UT, untreated. HK (hexokinase-derived peptide) serves as a positive control.
Figure 6A:
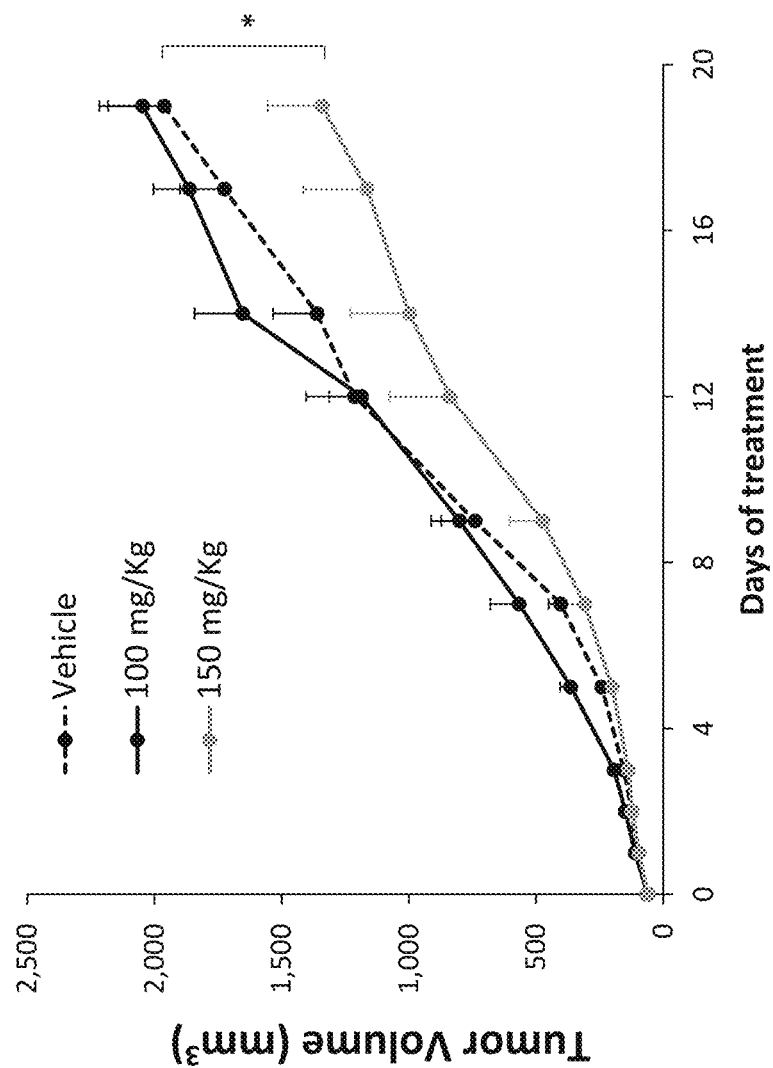
FIG. 6A. Formula C administration decreased tumor volume in Balb/C mice in syngeneic cancer model (CT26 mouse colorectal cancer).
Figure 6C:
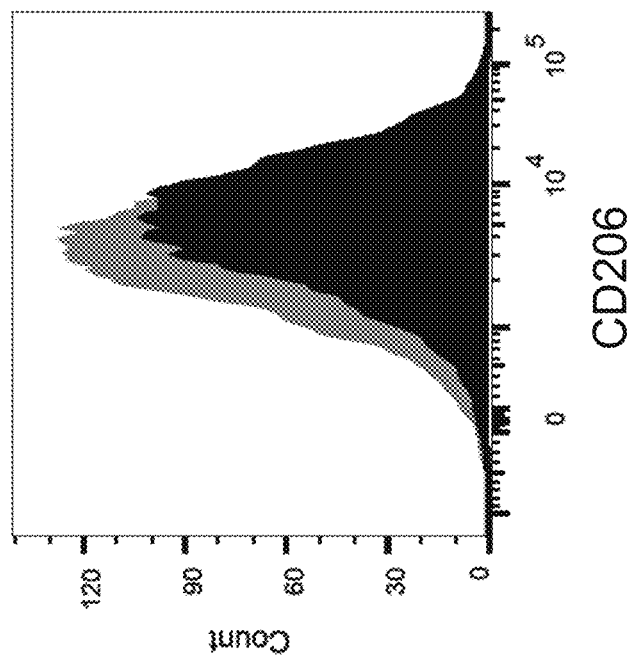
FIG. 6C. Formula C administration shifts macrophages in vivo from pro-tumor (M2) macrophages to antitumor (M1) macrophages. CT26 tumors from Formula C or vehicle-treated Balb/C mice with CT26 mouse colorectal cancer was analyzed for CD206. Dark color: Vehicle treated CT26 tumors from Balb/C mice (day 20). Light color: Formula C (150 mg/kg) treated CT26 tumors from Balb/C mice (day 20).
Figure 6B:
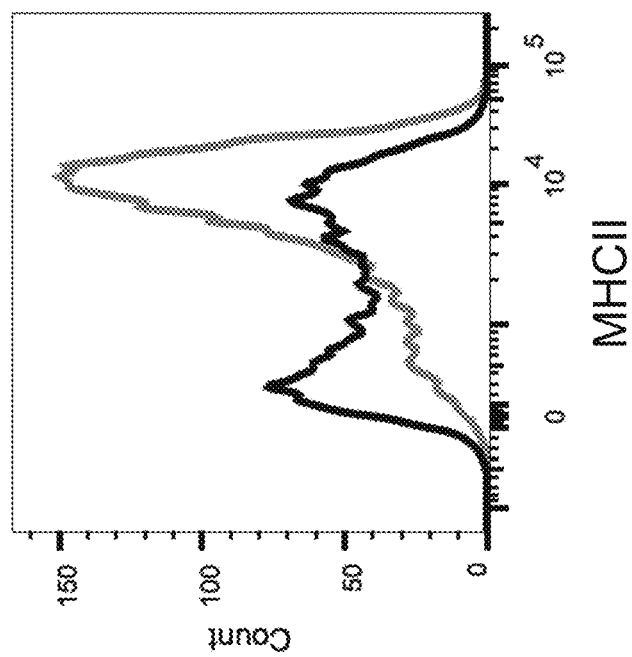
FIG. 6B. Formula C administration shifts macrophages in vivo from pro-tumor (M2) macrophages to antitumor (M1) macrophages. CT26 tumors from Formula C or vehicle-treated Balb/C mice with CT26 mouse colorectal cancer was analyzed for MHCII marker by FACS. Dark color: Vehicle treated CT26 tumors from Balb/C mice (day 20). Light color: Formula C (150 mg/kg) treated CT26 tumors from Balb/C mice (day 20).

Formula C dose-dependently elicited IL-1β secretion from primary activated ex vivo macrophages (FIGS. 5A, 5C). Formula C had little effect on cell viability, even at high dosage (FIGS. 5B, 5D). This strongly supports the hypothesis that Formula C activates the NLRP3 inflammasome which results in IL-1β secretion and stimulation of the immune system.

Colorectal cancer was induced in Balb/C mice using CT26 mouse colorectal cancer cells. Formula C was administered SC with esterase-inhibitor BNPP (IP).

Administration of Formula C decreased tumor volume in Balb/C mice in a syngeneic cancer model (CT26 mouse colorectal cancer (FIG. 6A)). Formula C administration shifts macrophages in vivo from pro-tumor (M2) macrophages to antitumor (M1) macrophages.

Pro-tumor M2 Macrophages are characterized by low MHCII and high CD206. In contrast, anti-tumor M1 Macrophages are characterized by high MHCII and low CD206. CT26 tumors from Formula C or vehicle-treated Balb/C mice with CT26 mouse colorectal cancer were analyzed for MHCII (FIG. 6B) and CD206 (FIG. 6C) levels 20 days after treatment started. The data demonstrated that Formula C-treated mice had higher MHCII levels and lower CD206 levels compared to vehicle-treated mice, indicating that Formula C treatment shifts macrophages in vivo from pro-tumor (M2) macrophages to antitumor (M1) macrophages.

Example 4

Formula C Treatment Shifted CD8+ T Cells from Effector T Cells to Memory T Cells Spleens from the 2 BALB/C female mice (8.5 weeks old) were injected with cold PBS in a 6 mm plate to obtain cell suspension, using a 27 g needle. The spleens were then crushed using the back of a 10 ml syringe. The suspension was passed through a 21 g needle and filtered using a 70 um cells strainer. The plate was washed once with 10 ml PBS and the solution was filtered as well. Cells were centrifuged for 10 min at 1200 rpm, 4° C. The pellet was broken on the grill and re-suspended in 10 ml AKC X1 lysis buffer (1:10 dilution of X10 stock in Ultra-Pure Water). After 5 min on ice, PBS was added to a final volume of 50 ml, and cells were centrifuged for 10 min at 1200 rpm, 4° C. Pellet was re-suspended in 10 ml PBS and washed twice. After washing, pellet was re-suspended in 20 ml DCs medium and passed through a 40 μm cell strainer. Cells were suspended to $3\times10^6$ ml with DC medium and supplemented with 1:1000 (100 Units/ml) hIL-2 and 1:1000 (1 ug/ml) anti-CD28.

The cells were seeded 1 ml/well in a 24-well plate precoated with 5 μg/ml 250 μl/well of anti-CD3e and carefully washed twice with 0.5 ml PBS (−/−), cells were added on the side of the wells to avoid washing away the antibody.

Splenocytes were plated at $10^6$ cells/well in a 24-well plate coated with 5 μg/ml anti-CD3e with soluble anti CD28 2 μg/ml and IL-2 100 units/ml. Cells were stimulated for 48 hours then reseeded 700,000 cells/well with the different compounds for 24 hours in the presence of IL-1 100 units/ml.

On the following day, cells were stained with: ghost dye 1 ul/sample (live/dead), and the following antibodies: CD62L, CD44, CD3, CD4, CD8 and analyzed by fluorescence-activated cell sorting (FACS).

Naïve, non-stimulated cells demonstrated high CD62L and low CD44 (FIG. 7A), while stimulated cells (vehicle, FIG. 7B, FIG. 7D) shifted to CD8+ effector phenotype (lower right quadrant) and memory cell phenotype (top right quadrant). Formula C treatment shifted stimulated T cells to higher CD44 and higher CD62L expression compared to vehicle-treated, signifying a shift from effector to memory cells (FIG. 7E). 2-DG treatment had a similar effect to Formula C (FIG. 7C). Neither Formula C nor 2-DG treatment significantly affected the percentage of live cells (FIG. 7F).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. A method of inducing an immune response or potentiating an immune response in a subject, the method comprising the step of contacting one or more cells of said subject with a therapeutically effective amount of a compound that promotes the detachment of Hexokinase 2 (HK2) from the mitochondria, wherein said compound is represented by the structure of Formula (IV)

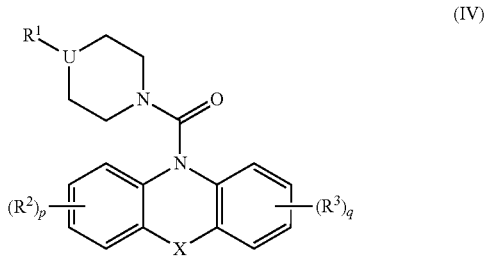

or wherein said compound is represented by a structure of Formula (VI)

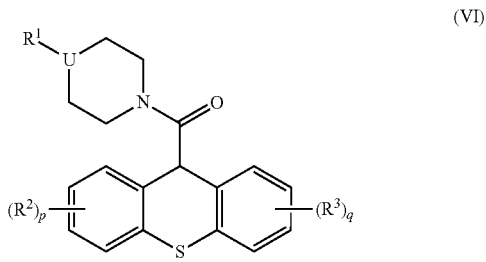

wherein

U is N or CH;

X is O;

$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$ or a combination thereof;

$R^2$ and $R^3$ are each independently at each occurrence selected from the group consisting of halogen, $NO_2$, CN, $C_1$-$C_4$ alkyl, $OR^4$, and $NR^{5a}R^{5b}$;

$R^4$, $R^a$, $R^{5a}$, and $R^{5b}$ are each independently hydrogen or $C_1$-$C_4$ alkyl;

p and q are each independently selected from 0, 1, 2, 3, and 4; or a pharmaceutically acceptable salt thereof.

2. The method of claim 1, wherein said immune response comprises conversion of macrophages from M2 to M1 phenotype, activation of an NLRP inflammasome, or a combination thereof.

3. The method of claim 1, wherein the induction of said immune response increases processing and/or secretion of interleukin (IL)-1β, IL-18, or a combination thereof.

4. The method of claim 1, wherein said immune response comprises a cellular immune response.

5. The method of claim 4, wherein said cellular immune response comprises activation of T-cells, shifting effector T cells to memory T cells, activation of mast cells, lowering myeloid-derived suppressor cell (MDSC) levels, activation of dendritic cells or a combination thereof.

6. The method of claim 5, wherein said dendritic cells are Langerin+ dendritic cells.

7. The method of claim 1, wherein said subject suffers from a hyperproliferative disorder.

8. The method of claim 7, wherein said hyperproliferative disorder is a cancer, a tumor, a pre-cancerous condition, or a benign hyperproliferative disorder.

9. The method of claim 7, wherein said benign hyperproliferative disorder is Ledderhose Disease, Dupuytren's Disease, a keloid, or a hypertrophic scar.

10. The method of claim 7, wherein said pre-cancerous condition is actinic keratosis or Bowen's Disease.

11. The method of claim 7, wherein said cancer is leukemia or a lymphoma.

12. The method of claim 11, wherein said leukemia is acute myeloid leukemia (AML), acute lymphocytic leukemia (ALL), or B-cell chronic lymphocytic leukemia (B-CLL).

13. The method of claim 11, wherein said lymphoma is a cutaneous T-cell lymphoma or a Non-Hodgkin lymphoma.

14. The method of claim 13, wherein the cutaneous T-cell lymphoma is mycosis fungoides or Sezary syndrome.

15. The method of claim 7, wherein said cancer is a colon cancer, a stomach cancer, a head and neck cancer, a breast cancer, a prostate cancer, a kidney cancer, a thyroid cancer, a skin cancer, a lung cancer, or a pancreatic cancer.

16. The method of claim 15, wherein said prostate cancer comprises metastatic castration resistant prostate cancer (CRPC).

17. The method of claim 15, wherein said breast cancer comprises triple negative breast cancer.

18. The method of claim 15, wherein said lung cancer is a non-small cell lung cancer (NSCLC) or a small cell lung cancer (SCLC).

19. The method of claim 15, wherein said skin cancer is a melanoma, a basal cell carcinoma or a squamous cell carcinoma.

20. The method of claim 1, wherein said subject is immunocompromised.

21. The method of claim 20, wherein said subject has an immunodeficiency disorder.

22. The method of claim 1, wherein said compound is present in a composition comprising a pharmaceutically acceptable carrier or excipient.

23. The method of claim 22, wherein—said composition is formulated for parenteral administration or for oral, intravenous, subcutaneous, or intramuscular administration.

24. The method of claim 22, wherein said composition is formulated for topical administration.

25. The method of claim 24, wherein said composition is formulated as an ointment, a cream, a lotion, a foam, a paste, or a gel.

26. The method of claim 25, wherein said composition is formulated as a 5%, 10%, 20%, 30%, 40% or 50% cream, gel, ointment or paste.

27. The method of claim 1, wherein said compound is formulated for oral administration.

28. The method of claim 1, wherein said compound is:
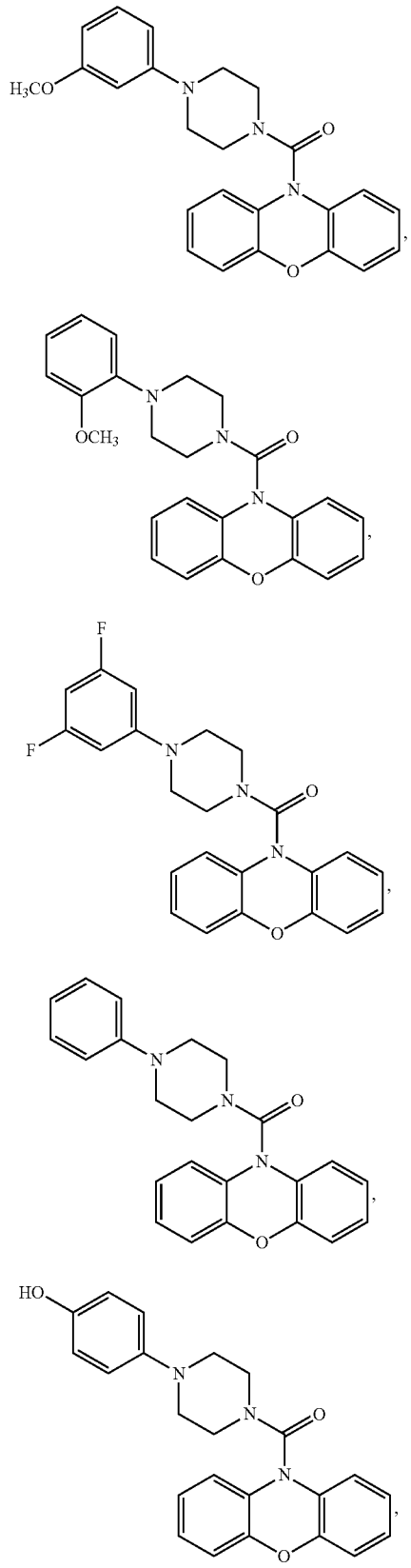
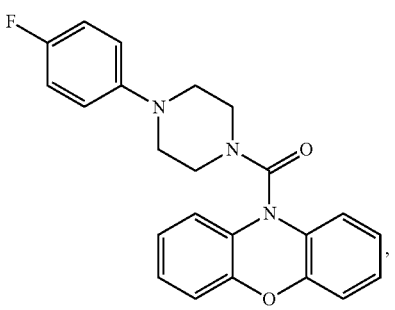
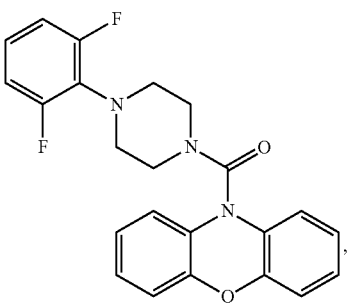
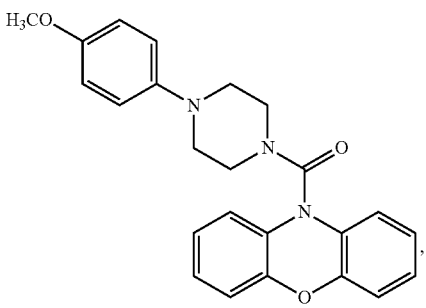
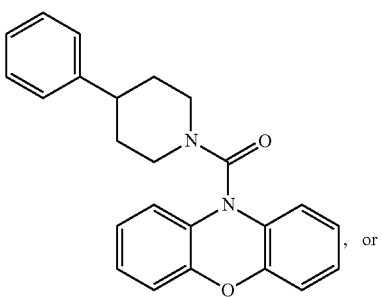
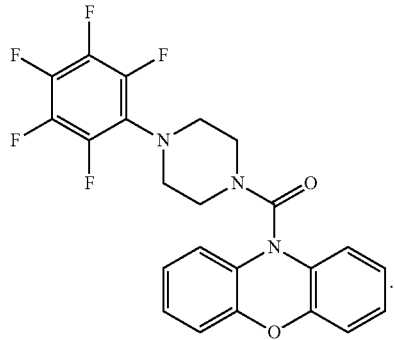

29. The method of claim 1, wherein said compound is:
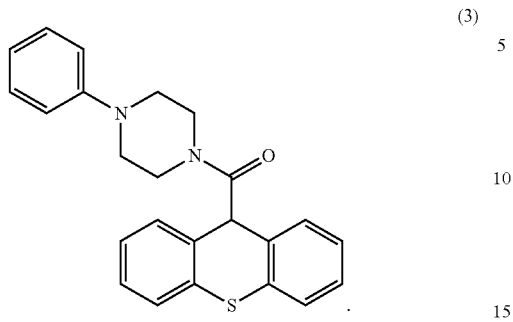
(3)
* * * * *